(12) United States Patent
Napier et al.

(10) Patent No.: US 7,714,185 B2
(45) Date of Patent: May 11, 2010

(54) METHOD FOR THE PRODUCTION OF POLYUNSATURATED FATTY ACIDS

(75) Inventors: Jonathan A. Napier, Herts (GB); Olga Sayanova, Hertfordshire (GB); Colin M. Lazarus, Bristol (GB); Baoxiu Qi, Bath (GB); Ernst Heinz, Hamburg (DE); Thorsten Zank, Mannheim (DE); Ulrich Zähringer, Ahrensburg (DE)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 10/539,891

(22) PCT Filed: Dec. 11, 2003

(86) PCT No.: PCT/EP03/14054

§ 371 (c)(1),
(2), (4) Date: Jun. 17, 2005

(87) PCT Pub. No.: WO2004/057001

PCT Pub. Date: Jul. 8, 2004

(65) Prior Publication Data
US 2006/0246556 A1 Nov. 2, 2006

(30) Foreign Application Priority Data

Dec. 19, 2002 (GB) .................... 0229578.0
Jul. 21, 2003 (GB) .................... 0316989.3

(51) Int. Cl.
C12N 15/82 (2006.01)
C12N 15/87 (2006.01)
C07H 21/04 (2006.01)

(52) U.S. Cl. .................... 800/281; 800/278; 536/23.2
(58) Field of Classification Search ............... None
See application file for complete search history.

(56) References Cited

U.S. PATENT DOCUMENTS

| | | | |
|---|---|---|---|
| 5,614,393 A | 3/1997 | Thomas et al. | |
| 5,968,791 A | 10/1999 | Davies et al. | |
| 6,043,411 A | 3/2000 | Nishizawa et al. | |
| 6,677,145 B2 * | 1/2004 | Mukerji et al. | 435/193 |
| 6,825,017 B1 * | 11/2004 | Browse et al. | 435/190 |
| 2002/0138874 A1 | 9/2002 | Mukerji et al. | |
| 2004/0049805 A1 | 3/2004 | Lerchl et al. | |

FOREIGN PATENT DOCUMENTS

| | | |
|---|---|---|
| EP | 0 550 162 | 7/1993 |
| EP | 0 794 250 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/27203 | 6/1998 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-98/55625 | 12/1998 |
| WO | WO-99/27111 | 6/1999 |
| WO | WO-99/64616 | 12/1999 |
| WO | WO-00/18889 | 4/2000 |
| WO | WO-00/21557 | 4/2000 |
| WO | WO-00/34439 | 6/2000 |
| WO | WO-00/42195 | 7/2000 |
| WO | WO-02/057464 A2 | 7/2002 |
| WO | WO-02/077213 | 10/2002 |

OTHER PUBLICATIONS

Sayanova et al. 2006, FEBS Letters 580:1946-1952.*
McKeon T. et al., "Acyl-Acyl Carrier Protein Thioesterase From Safflower", Methods in Enzymology, 1981, vol. 71, Part C (Lipids), pp. 178-180.
McKeon T. et al., "Stearoyl-Acyl Carrier Protein Desaturase From Safflower Seeds", Methods in Enzymology, 1981, vol. 71, pp. 275-281.
Abbadi et al., "Transgenic Oilseeds As Sustainable Source of Nutritionally Relevant C20 and C22 Polyunsaturated Fatty Acids?", Eur. J. Lipid Sci. Technol. 103 (2001), pp. 106-113.

(Continued)

Primary Examiner—Anne Kubelik
Assistant Examiner—Li Zheng
(74) Attorney, Agent, or Firm—Connolly Bove Lodge & Hutz, LLP

(57) ABSTRACT

The present invention relates to an improved process for the specific production of poly-unsaturated omega-3 and omega-6 fatty acids and a process for the production of triglycerides having an increased content of unsaturated fatty acids, in particular omega-3 and omega-6 fatty acids having at least two double bonds and a 20 or 22 carbon atom chain length. The invention relates to the production of a transgenic organism, preferably a transgenic plant or a transgenic microorganism, hav-ing an increased content of fatty acids, oils or lipids containing C20- or C22-fatty acids with a delta-5, 7, 8, 10 double bond, respectively due to the expression of a delta-8-desaturase and a delta-9-elon-gase from organisms such as plants preferably Algae like *Isochrysis galbana* or *Euglena gracilis*. In addition the invention relates to a process for the production of poly unsaturated fatty acids such as Eicosapentaenoic, Arachidonic, Docosapentaenoic or Doosahexaenoic acid through the co-expression of a delta-8-desaturase, a delta-9-elongase and a delta-5 desaturase in organisms such as microorganisms or plants. The invention additionally relates to the use of specific nucleic acid sequences encoding for the aforementioned proteins with delta-8-desaturase-, delta-9-elongase- or delta-5-desaturase-activity, nucleic acid constructs, vectors and organisms containing said nucleic acid sequences. The invention further relates to unsaturated fatty acids and triglycerides having an increased content of at least 1% by weight of unsaturated fatty acids and use thereof.

26 Claims, 6 Drawing Sheets

OTHER PUBLICATIONS

Akermoun et al., "Complex Lipid Biosynthesis: Phospholipid Synthesis", Biochemical Society Transactions 28 (2000), pp. 713-715.

Becker et al., "New Plant Binary Vectors With Selectable Markers Located Proximal To The Left T-DNA Border", Plant Molecular Biology 20 (1992), pp. 1195-1197.

Cases et al., "Identification Of A Gene Encoding An Acyl CoA:Diacylglycerol Acyltransferase, A Key Enzyme in Triacylglycerol Synthesis", Proc. Natl. Acad. Sci. USA 95 (1998), pp. 13018-13023.

Fraser et al., "Partial Purification and Photoaffinity Labelling of Sunflower Acyl-CoA:Lysophosphatidylcholine Acyltransferase", Biochemical Society Transactions 28 (2000), pp. 715-718.

Frentzen, M., "Acyltransferases From Basic Science to Modified Seed Oils", Fett/Lipid 100 (1998), pp. 161-166.

Wallis et al., "Euglena gracilis delta8 Fatty Acid Desaturase (efd1) mRNA, Complete cds", GenBank AF139720/AAD45877, Jul. 30, 1999.

Huang et al., "Cloning of Δ12- and Δ6-Desaturases From *Mortierella alpina* and Recombinant Production of γ-Linolenic Acid in *Saccharomyces cerevisiae*", Lipids 34, 7 (1999), pp. 649-659.

Knutzon et al., "Cloning of a Coconut Endosperm cDNA Encoding a 1-Acyl-*sn*-Glycerol-3-Phosphate Acyltransferase That Accepts Medium-Chain-Length Substrates", Plant Physiol. 109 (1995), pp. 999-1006.

Lands, W. E. M., "Metabolism of Glycerolipids. II. The Enzymatic Acylation Of Lysolecithin", The Journal of Biological Chemistry, 235, 8 (1960), pp. 2233-2237.

Metz et al., "Production of Polyunsaturated Fatty Acids by Polyketide Synthases in Both Prokaryotes and Eukaryotes", Science 293 (2001), pp. 290-293.

Mikolajczak et al., "Search for New Industrial Oils. V. Oils of Cruciferae", Journal of the American Oil Chemists' Society 38 (1961), pp. 678-681.

Qi et al., "Identification of a cDNA Encoding a Novel C18-Δ$^9$ Polyunsaturated Fatty Acid-Specific Elongating Activity From The Docosahexaenoic Acid (DHA)-Producing Microalga, *Isochrysis galbana*", FEBS Letters 510 (2002), pp. 159-165.

Slabas et al., "Acyltransferases And Their Role In The Biosynthesis of Lipids-Opportunities For New Oils", J. Plant Physiol. 158 (2001), pp. 505-513.

Stukey et al., "The *OLE1* Gene Of *Saccharomyces cerevisiae* Encodes The Δ9 Fatty Acid Desaturase And Can Be Functionally Replaced By The Rat Stearoyl-CoA Desaturase Gene", The Journal of Biological Chemistry 265, 33 (1990), pp. 20144-20149.

Stymne et al., "Evidence for the Reversibility of the Acyl-CoA: Lysophosphatidylcholine Acyltransferase In Microsomal Preparations From Developing Safflower (*Carthamus tinctorius* L.) Cotyledons And Rat Liver", Biochem. J. 223 (1984), pp. 305-314.

Tumaney et al., "Synthesis of Azidophospholipids And Labeling of Lysophosphatidylcholine Acyltransferase From Developing Soybean Cotyledons", Biochimica et Biophysica Acta 1439 (1999), pp. 47-56.

Wada et al., "Enhancement Of Chilling Tolerance Of A Cyanobacterium By Genetic Manipulation Of Fatty Acid Desaturation", Nature 347 (1990), pp. 200-203.

Wallis et al., "The Δ$^8$-Desaturase of *Euglena gracilis*: An Alternate Pathway For Synthesis Of 20-Carbon Polyunsaturated Fatty Acids", Archives of Biochemistry and Biophysics 365 (1999), pp. 307-316.

Wang et al., "Biosynthesis and Regulation of Linolenic Acid in Higher Plants", Plant Physiol. Biochem. 26, 6 (1988), pp. 777-792.

Yamashita et al., "ATP-Independent Fatty Acyl-Coenzyme A Synthesis From Phospholipid", The Journal of Biological Chemistry 276, 29 (2001), pp. 26745-26752.

Zank et al. "Cloning And Functional Expression Of The First Plant Fatty Acid Elongase Specific For Δ$^6$-Polyunsaturated Fatty Acids", Biochemical Society Transactions 28 (2000), pp. 654-658.

Mishra et al. "Purification And Characterization Of Thiol-Reagent-Sensitive Glycerol-3-Phosphate Acyltransferase From The Membrane Fraction Of An Oleaginous Fungus", Biochem. J. 355 (2001), pp. 315-322.

\* cited by examiner

METHOD FOR THE PRODUCTION OF POLYUNSATURATED FATTY ACIDS

RELATED APPLICATIONS

This application is a national stage application (under 35 U.S.C. 371) of PCT/EP2003/014054 filed Dec. 11, 2003 which claims benefit to Great Britain application 0229578.0 filed Dec. 19, 2002 and Great Britain application 0316989.3 filed Jul. 23, 2003.

FIELD OF THE INVENTION

The present invention relates to an improved process for the specific production of poly-unsaturated ω-3 and ω-6 fatty acids and a process for the production of triglycerides having an increased content of unsaturated fatty adds, in particular ω-3 and ω-6 fatty acids having at least two double bonds and a 20 or 22 carbon atom chain length. The invention relates to the production of a transgenic organism, preferably a transgenic plant or a transgenic microorganism, having an increased content of fatty acids, oils or lipids containing $C_{20}$- or $C_{22}$-fatty acids with a Δ 5, 7, 8, 10 double bond, respectively due to the expression of a Δ 8-desaturase and a Δ 9-elongase from organisms such as plants preferably Algae like *Isochrysis galbana* or *Euglena gracilis*. In addition the invention relates to a process for the production of poly unsaturated fatty acids such as Eicosapentaenoic, Arachidonic, Docosapentaenoic or Docosahexaenoic acid through the co-expression of a Δ-8-desaturase, a Δ-9-elongase and a Δ-5 desaturase in organisms such as microorganisms or plants.

The invention additionally relates to the use of specific nucleic acid sequences encoding for the aforementioned proteins with Δ-8-desaturase-, Δ-9-elongase- or Δ-5-desaturase-activity, nucleic acid constructs, vectors and organisms containing said nucleic acid sequences. The invention further relates to unsaturated fatty adds and triglycerides having an increased content of at least 1% by weight of unsaturated fatty acids and use thereof.

DESCRIPTION OF RELATED ART

Fatty acids and triglycerides have numerous applications in the food industry, animal nutrition, cosmetics and in the drug sector. Depending on whether they are free saturated or unsaturated fatty acids or triglycerides with an increased content of saturated or unsaturated fatty acids, they are suitable for the most varied applications; thus, for example, polyunsaturated fatty acids (=PUFAs) are added to infant formula to increase its nutritional value. The various fatty acids and triglycerides are mainly obtained from microorganisms such as *Mortierella* or from oil-producing plants such as soybean, oilseed rape, sunflower and others, where they are usually obtained in the form of their triacylglycerides. Alternatively, they are obtained advantageously from animals, such as fish. The free fatty acids are prepared advantageously by hydrolysis.

Whether oils with unsaturated or with saturated fatty acids are preferred depends on the intended purpose; thus, for example, lipids with unsaturated fatty acids, specifically polyunsaturated fatty acids, are preferred in human nutrition since they have a positive effect on the cholesterol level in the blood and thus on the possibility of heart disease. They are used in a variety of dietetic foodstuffs or medicaments. In addition PUFAs are commonly used in food, feed and in the cosmetic industry. Poly unsaturated ω-3- and/or ω-6-fatty acids are an important part of animal feed and human food. Because of the common composition of human food poly unsaturated ω-3-fatty acids, which are an essential component of fish oil, should be added to the food to increase the nutritional value of the food; thus, for example, poly unsaturated fatty acids such as Docosahexaenoic acid (=DHA, $C_{22:5}^{\Delta 4,7,10,13,16,19}$) or Eicosapentaenoic acid (=EPA, $C_{20:5}^{\Delta 5,8,11,14,17}$) are added as mentioned above to infant formula to increase its nutritional value. Whereas DHA has a positive effect of the brain development of babies. The addition of poly unsaturated ω-3-fatty acids is preferred as the addition of poly unsaturated ω-6-fatty acids like Arachidonic acid (=ARA, $C_{220:4}^{\Delta 5,8,11,14}$) to common food have an undesired effect for example on rheumatic diseases such as rheumatoid arthritis. Poly unsaturated ω-3- and ω-6-fatty acids are precursor of a family of paracrine hormones called eicosanoids such as prostaglandins which are products of the metabolism of Dihomo-γ-linoleic acid, ARA or EPA. Eicosanoids are involved in the regulation of lipolysis, the initiation of inflammatory responses, the regulation of blood circulation and pressure and other central functions of the body. Eicosanoids comprise prostaglandins, leukotrienes, thromboxanes, and prostacyclins. ω-3-fatty acids seem to prevent artherosclerosis and cardiovascular diseases primarily by regulating the levels of different eicosanoids. Other Eicosanoids are the thromboxanes and leukotrienes which are products of the metabolism of ARA or EPA.

Principally microorganisms such as Mortierella or oil producing plants such as soybean, rapeseed or sunflower or algae such as *Crytocodinium* or *Phaeodactylum* are a common source for oils containing PUFAs, where they are usually obtained in the form of their triacyl glycerides. Alternatively, they are obtained advantageously from animals, such as fish. The free fatty acids are prepared advantageously by hydrolysis with a strong base such as potassium or sodium hydroxide. Higher poly unsaturated fatty acids such as DHA, EPA, ARA, Dihomo-γ-linoleic acid ($C_{20:3}^{66\ 8,11,14}$) or Docosapentaenoic acid (=DPA, $C_{22:5}^{\Delta 7,10,13,16,19}$) are not produced by oil producing plants such as soybean, rapeseed, safflower or sunflower. A natural sources for said fatty acids are fish for example herring, salmon, sardine, redfish, eel, carp, trout, halibut, mackerel, pikeperch or tuna or algae.

On account of their positive properties there has been no shortage of attempts in the past to make available genes which participate in the synthesis of fatty acids or triglycerides for the production of oils in various organisms having a modified content of unsaturated fatty acids. Thus, in WO 91/13972 and its US equivalent a Δ-9-desaturase is described. In WO 93/11245 a Δ-15-desaturase and in WO 94/11516 a Δ-12-desaturase is claimed. WO 00/34439 discloses a Δ-5- and a Δ-8-desaturase. Other desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. To date, however, the various desaturases have been only inadequately characterized biochemically since the enzymes in the form of membrane-bound proteins are isolable and characterizable only with very great difficulty (McKeon et al., Methods in Enzymol. 71,1981: 12141-12147, Wang et al., Plant Physiol. Biochem., 26,1988: 777-792). Generally, membrane-bound desaturases are characterized by introduction into a suitable organism which is then investigated for enzyme activity by means of analysis of starting materials and products. Δ-6-Desaturases are described in WO 93/06712, U.S. Pat. No. 5,614,393, U.S. Pat. No. 5,614,393, WO 96/21022, WO0021557 and WO 99/27111 and their application to production in transgenic organisms is also described, e.g. in WO 9846763, WO 9846764 and WO 9846765. At the same time the expression of various fatty acid biosynthesis genes, as in WO 9964616 or WO 9846776, and the formation of poly-unsaturated fatty acids is also described and claimed.

With regard to the effectiveness of the expression of desaturases and their effect on the formation of polyunsaturated fatty acids it may be noted that through expression of a desaturases and elongases as described to date only low contents of poly-unsaturated fatty acids/lipids, such as by way of example eicosapentaenoic or arachidonic acid, have been achieved. Therefore, an alternative and more effective pathway with higher product yield is desirable.

Accordingly, there is still a great demand for new and more suitable genes which encode enzymes which participate in the biosynthesis of unsaturated fatty acids and make it possible to produce certain fatty acids specifically on an industrial scale without unwanted byproducts forming. In the selection of genes for biosynthesis two characteristics above all are particularly important. On the one hand, there is as ever a need for improved processes for obtaining the highest possible contents of polyunsaturated fatty acids.

DETAILED DESCRIPTION OF THE INVENTION

Figure 1:
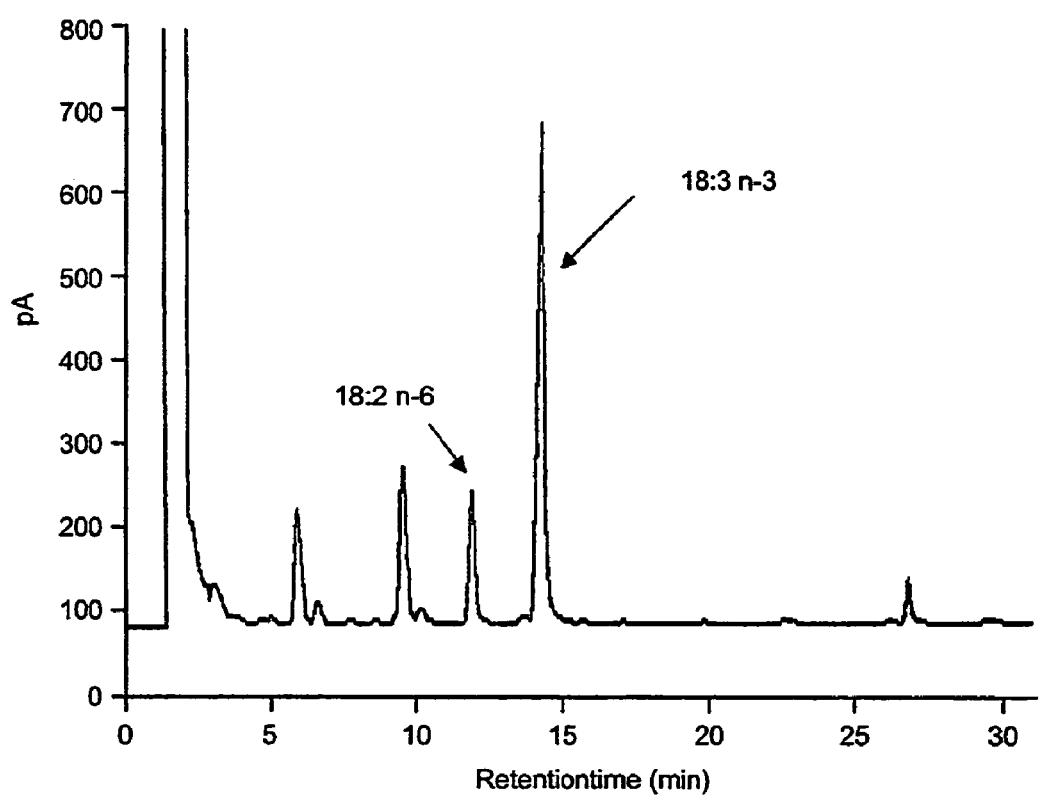
FIG. 1 shows the fatty acid profile (FAMes) of leaf tissue from wild type *Arabidopsis thaliana* as a control.

Accordingly, it is an object of the present invention to provide further genes of desaturase and elongase enzymes for the synthesis of polyunsaturated fatty acids in organisms preferably in microorganisms and plants and to use them in a commercial process for the production of poly unsaturated fatty acids. Said process should increase PUFA content in organisms as much as possible preferably in seeds of an oil producing plant.

We have found that this object is achieved by a process for the production of compounds of the following general formula

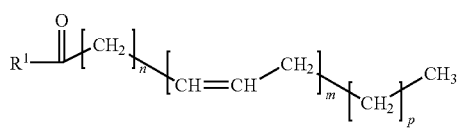
(I)

in transgenic organisms with a content of at least 1% by weight of said compounds referred to the total lipid content of said organism which comprises the following steps:

a) introduction of at least one nucleic acid sequence in a transgenic organism, which encodes a Δ-9-elongase, and
b) introduction of at least one second nucleic acid sequence which encodes a Δ-8-desaturase, and
c) if necessary introduction of at least a one third nucleic acid sequence, which encodes a Δ-5-desaturase, and
d) cultivating and harvesting of said organism; and where the variables and substituents in formula I have the following meanings:
$R^1$=hydroxyl-, Coenzyme A-(Thioester), phosphatidylcholine-, phosphatidylethanol-amine-, phosphatidylglycerol-, diphosphatidylglycerol-, phosphabdyiserine-, phosphatidylinositol-, sphingoflipid-, glycoshingolipid- or a residue of the general formula II:

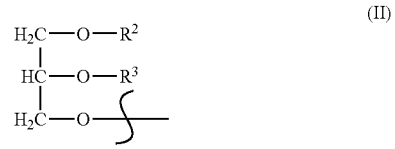
(II)

where the substituents in formula II have the following meanings:
$R^2$=hydrogen-, phosphatidylcholine-, phosphatidylethanolamine-, phosphatidyglycerol-, diphosphatidylglycerol-, phosphahdyiserine-, phosphatidylinositol-, shingolipid-, glycoshingolipid-, glycoshingolipid- or saturated or unsaturated $C_2$-$C_{24}$-alkylcarbonyl-,
$R^3$ =hydrogen-, saturated or unsaturated $C_2$-$C_{24}$-alkylcarbonyl-, or
$R^2$ and $R^3$ independent of each other a residue of the formula Ia:

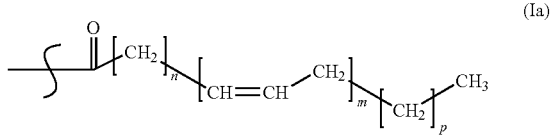
(Ia)

n=3,4 or 6, m=3, 4 or 5 and p=0 or 3, preferably n=3, m=4 or 5 and p=0 or 3.
$R^1$ indicates in the formula I hydroxyl-, Acetyl-Coenzyme A-, phosphatidylcholine-, phosphatidylethanolamine-, phosphatidylglycerol-, diphosphatidylglyoerol-, phosphatidylserine-, phosphatidyrinositol-, sphingolipid-, glycoshingolipid- or a residue of the general formula II

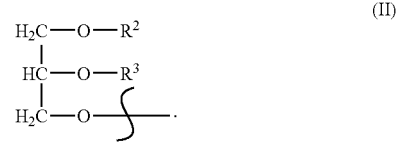
(II)

The abovementioned residues for $R^1$ are always coupled to compounds of the general formula I in the form of their ester or thioester.

$R^2$ indicates in structures of the general formula II hydrogen, phosphatidylcholine-, phosphatidylethanolamine-, phosphatidylglycerol-, diphosphatidylglycerol-, phosphatidylserine-, phosphatidylinositol-, shingolipid-, glycoshingolipid-, glycoshingolipid- or saturated or unsaturated $C_2$-$C_{24}$-alkylcarbonyl-residues, Alkyl radicals which may be mentioned are substituted or unsubstituted, saturated or unsaturated $C_2$-$C_{24}$-alkylcarbonyl-chains such as ethylcarbonyl-, n-propylcarbonyl-, n-butylcarbonyl-, n-pentylcarbonyl-, n-hexylcarbonyl-, n-heptylcarbonyl-, n-octylcarbonyl-, n-nonylcarbonyl-, n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-, that contain one or more double bonds. Saturated or unsaturated $C_{10}$-$C_{22}$-Alkylcarbonylresidues such as n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-are preferred, which contain one ore more double bonds. In particular privileged are saturated or unsaturated $C_{10}$-$C_{22}$-alkylcarbonyl-residue as $C_{10}$-alkylcarbonyl-, $C_{11}$-alkylcarbonyl-, $C_{12}$-alkylcarbonyl-, $C_{13}$-alkylcarbonyl-, $C_{14}$-alkylcarbonyl-, $C_{16}$-alkylcarbonyl-, $C_{18}$-alkylcarbonyl-, $C_{20}$-alkylcarbonyl-, $C_{22}$-alkylcarbonyl- or $C_{24}$-alkylcarbonyl-residue, that contain one ore more double bonds. In particular privileged are saturated or unsaturated $C_{16}$-$C_{22}$-alkylcarbonyl-residue as $C_{16}$-alkylcarbonyl-, $C_{18}$-alkylcarbonyl-, $C_{20}$-alkylcarbonyl- or $C_{22}$-alkylcarbonyl-residue, that contain one ore more double bonds. The residues contain in particular two, three, four or five double bonds. Particularly preferred are residues of 20 or 22 carbon atoms having up to five double bonds, preferably three, four or five double bonds. All residues are derived from the mentioned corresponding fatty acids.

$R^3$ indicates in structures of the general formula II hydrogen, saturated or unsaturated $C_2$-$C_{24}$-alkylcarbonyl.

Substituted or unsubstituted, saturated or unsaturated $C_2$-$C_{24}$-alkylcarbonyl-residues are e.g. ethylcarbonyl-, n-propylcarbonyl-, n-butylcarbonyl-, n-pentylcarbonyl-, n-hexylcarbonyl-, n-heptylcarbonyl-, n-octylcarbonyl-, n-nonylcarbonyl-, n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-, having one or more double bonds. Preferred are saturated or unsaturated $C_{10}$-$C_{24}$-alkylcarbonyl residues as n-decylcarbonyl-, n-undecylcarbonyl-, n-dodecylcarbonyl-, n-tridecylcarbonyl-, n-tetradecylcarbonyl-, n-pentadecylcarbonyl yl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-, with one ore more double bonds. In particular saturated or unsaturated $C_{10}$-$C_{24}$-alkylcarbonyl residues as $C_{10}$-alkylcarbonyl-, $C_{11}$-alkylcarbonyl-, $C_{12}$-alkylcarbonyl-, $C_{13}$-alkylcarbonyl-, $C_{14}$-alkylcarbonyl, $C_{16}$-alkylcarbonyl-, $C_{18}$-alkylcarbonyl-, $C_{20}$-alkylcarbonyl-, $C_{22}$-alkylcarbonyl- or $C_{24}$-alkylcarbonyl-residues with one or more double bonds. In particular preferred are saturated or unsaturated $C_{16}$-$C_{22}$-alkylcarbonyl-residue as $C_{16}$-alkylcarbonyl-, $C_{18}$-alkylcarbonyl-, $C_{20}$-alkylcarbonyl- or $C_{22}$-alkylcarbonyl-residues, with multiple double bonds. $C_{18}$-alkylcarbonyl-residues are particularly preferred, which contain one, two, three or four double bonds and $C_{20}$-alkylcarbonyl-residues, with three, four or five double bonds. All residues are derived from the corresponding fatty acids.

$R^2$ and $R^3$ indicates in structures of the general formula II independent of each other a residue of the general formula Ia

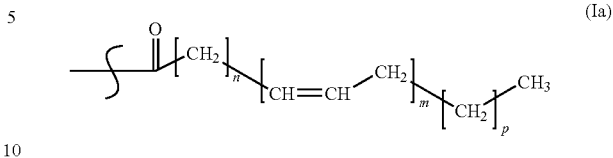

(Ia)

whereas the variables in the formula I and Ia are defined as: n=3,4 or 6, m=3, 4 or 5 and p=0 or 3. In particular n=3, m=4 or 5 and p=0 or 3.

The abovementioned residues $R^1$, $R^2$ and $R^3$ can be substituted with hydroxyl- or epoxy-groups or might contain also triple bonds.

According to the invention the used nucleic acid sequences are isolated nucleic sequences coding for polypeptides having $C_{20}$-$\Delta 5$- or $\Delta$-8 desaturase or $C_{18}$-$\Delta 9$-elongase activity.

The according to inventive process synthesized substances of formula I which contain as residue $R^1$ the residue of formula II contain preferentially a mixture of different residues $R^2$ or $R^3$. The residues are derived from different fatty acid molecules as short chain fatty acids with 4 to 6 C-atoms, mid-chain fatty acids having 8 to 12 C-atoms and long-chain fatty acids with 14 to 24 C-atoms, whereas the long-chain fatty acids are preferred. Said long chain fatty acids are derived preferentially from $C_{18}$- or $C_{20}$-poly unsaturated fatty acids having advantageously between two and five double bonds. In addition the backbone of formula I is also derived from such a aforementioned fatty acid which advantageously is also different from $R^2$ and $R^3$. That means compounds which are produced by the inventive process are in one aspect of the invention triglycerides of different substituted or unsubstituted, saturated or unsaturated fatty acid ester or thioesters.

According to another aspect of the invention poly-unsaturated fatty acid esters (of the formula I) with 18, 20 or 22 fatty acid carbon atoms chain length with at least two double bonds, preferably three, four or five are particularly preferred.

In particular fatty add molecules with three, four or five double bonds are preferred for the synthesis of eicosadienoic, eicosatrienoic, eicosatetranoic (arachidonic-acid) and eicosapentanoic acid (C20:2n-6, $\Delta$11, 14; C20:3n-6, $\Delta$8, 11, 14; C20:4n-6, $\Delta$5, 8, 11, 14, C20:3n-3, $\Delta$11, 14, 17; C20:4n-3, $\Delta$8, 11, 14, 17; C20:5n-3, $\Delta$5, 8, 11, 14, 17) in the inventive process, whereas arachidonic add and eicosapentaenoic acid are most preferred. We have found that this object is advantageously achieved by the combined expression of three isolated nucleic acid sequences according to the invention which encode for polypeptides having the following activities: a polypeptides with C20-$\Delta$-8-desaturase activity, a C18-$\Delta$-9-elongase activity, and a C20-$\Delta$-5 desaturase activity. This objective was achieved in particular by the co-expression of the isolated nucleic acid sequences according to the invention. C18 fatty acids with a double bond in $\Delta$-9-position are elongated by the $\Delta$-9-elongase advantageously used in the inventive process. By the $\Delta$-8-desaturase used in the process a double in $\Delta$-8-position is introduced into C20 fatty acids. In addition a double bond can be introduced into the fatty acid molecules in $\Delta$-5-position by the $\Delta$-5-desaturase.

The fatty acid ester of $C_{18}$-, $C_{20}$- and/or $C_{22}$-poly unsaturated fatty acids synthesized in the inventive process advantageously in form of their triglycerides as ester or thioesters can be isolated from the producing organism for example from a microorganism or a plant in the form of an oil, lipid or lipid mixture for example as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, or as monoacylglyceride, diacylglyceride or triacylglyceride or as other fatty acid esters such as acetyl-Coenzyme A thioester, which contain saturated or unsaturated fatty acids preferably poly unsaturated fatty acids with at least two preferably at least three double bonds in the fatty acid molecule. In addition to the in form of the aforementioned esters bound fatty acids also fatty acids bound in other compounds can be produced or also free fatty acids can be produced by the inventive process.

In general the transgenic organisms for example transgenic microorganisms or plants used in the inventive process contain fatty acid esters or fatty acids in a distribution of nearly 80 to 90% by weight of triacyl glycerides, 2 to 5% by weight diacyl glycerides, 5 to 10% by weight monoacyl glycerides, 1 to 5% by weight free fatty acids and 2 to 8% by weight phospholipids, whereas the total amount of the aforementioned compounds are all together a 100% by weight.

In the inventive process(es) [the singular shall include the plural and vice versa] at least 1% by weight, preferably at least 2, 3, 4 or 5% by weight, more preferably at least 6, 7, 8, or 9% by weight, most preferably 10, 20 or 30% by weight of the compounds of formula I referred to the total lipid content of the organism used in the process are produced. Preferred starting material for the inventive process are linoleic acid (C18:2) and/or linolenic acid (C18:3) which are transformed to the preferred end products ARA or EPA. As for the inventive process organisms are used the product of the process is not a product of one pure substance per se. It is a mixture of different substances of formula I where one or more compounds are the major product and others are only contained as side products. In the event that in an organism used in the process linoleic and linolenic acid are available the end product is a mixture of ARA and EPA. Advantageously the side products shall not exceed 20% by weight referred to the total lipid content of the organism, preferably the side products shall not exceed 15% by weight, more preferably they shall not exceed 10% by weight, most preferably they shall not exceed 5% by weight. Preferably organisms are used in the process which contain as starting material either linoleic or linolenic acid so that as end product of the process only ARA or EPA are produced. In the event EPA and ARA are produced together, they should be produced in a ratio of at least 1:2 (EPA-ARA), preferably of at least 1:3, more preferably of at least 1:4, most preferably of at least 1:5. In the event that a mixture of different fatty acids such as ARA and EPA are the product of the inventive process said fatty acids can be further purified by method known by a person skilled in the art such as distillation, extraction, crystallization at low temperatures, chromatography or a combination of said methods.

Advantageously the invented method comprise the following steps:
a) expression of at least one nucleic acid sequence in a plant that codes for an enzyme having Δ-9 elongase activity, and
b) expression of at least one nucleic acid sequences which codes for a C20-specific Δ-8 desaturase, and
c) possibly the expression of a third nucleic acid sequence which codes for a C20-specific Δ-5 desaturase
d) followed by the cultivation of the transgenic plants and seed harvest.

In principle all host organisms can be used in the inventive process for example transgenic organisms such as plants like mosses; green, red, brown or blue algae; monocotyledons or dicotyledones. Advantageously oil producing transgenic organisms such as fungi, bacteria, algae, mosses or plants are used in the inventive processes described herein (for the invention the singular shall include the plural and vice versa), Additional advantageously organisms are animals or preferably plants or parts thereof. Fungi, yeasts or plants are preferably used, particularly preferably fungi or plants, very particularly preferably plants such as oilseed plants containing high amounts of lipid compounds such as rapeseed, poppy, mustard, hemp, castor bean, sesame, olive, calendula, punica, hazel nut, almond, macadamia, avocado, pumpkin, walnut, laurel, pistachio, primrose, canola, peanut, linseed, soybean, safflower, sunflower, borage or plants such as maize, wheat, rye, oat, triticale, rice, barley, cotton, manihot, pepper, tagetes, solanaceaous plants such as potato, tobacco, eggplant, and tomato, Vicia species, pea, alfalfa, bushy plants (coffee, cacao, tea), Salix species, trees (oil palm, coconut) and perennial grasses and forage crops. Particularly preferred plants of the invention are oilseed plants rapeseed, poppy, mustard, hemp, castor bean, sesame, olive, calendula, punica, hazel nut, almond, macadamia, avocado, pumpkin, laurel, pistachio, primrose, canola, peanut, linseed, soybean, safflower, sunflower, borage or trees (oil palm, coconut). Most preferred are $C_{18:2}$- and/or $C_{18:3}$-fatty acid rich plants such as hemp, sesame, linseed, poppy, pumpkin, walnut, tobacco, cotton, safflower or sunflower.

Depending on the nucleic acid and/or the organism used in the inventive processes different compounds of the general formula I can be synthesized. In addition depending on the plant or fungi used in the process different mixtures of formula I compounds or single compounds such as arachidonic acid or eicosapentaenoic acid in free or bound form can be produced. In the event that in the inventive processes organism are used which have as precursor of the fatty acid synthesis preferably $C_{18:2}$- or $C_{18:3}$-fatty acids different poly unsaturated fatty acids can be synthesized for example starting from $C_{18:2}$-fatty acids γ-linoleic acid, dihomo-γ-linoleic acid or arachidonic acid can be produced or starting from $C_{18:3}$-fatty acids stearidonic acid, eicosatetraenoic acid or eicosapentaenoic acid can be produced. By influencing the activity of the different genes or their gene products different single compounds or compound mixtures can be produced. As living organisms are used in the inventive process the crude material that means crude lipids and/or oils isolated from the organisms preferably contain at least some starting compounds such as $C_{18:2}$- or $C_{18:3}$-fatty acids or their combination in the product and depending on the activity of the nucleic acid sequences and their gene products fatty acid intermediates of the biosynthesis chain. Said starting compounds or intermediates are in the product in a concentration of less than 20 or 15% by weight, preferably less than 10, 9, 8, 7 or 6% by weight, more preferably less than 5, 4, 3, 2 or 1% by weight of the total fatty acids isolated from the used organism.

Transgenic plants are to be understood as meaning single plant cells and their cultures on solid media or in liquid culture, parts of plants and entire plants such as plant cell cultures, protoplasts from plants, callus cultures or plant tissues such as leafs, shoots, seeds, flowers, roots etc. Said transgenic plants can be cultivated for example on solid or liquid culture medium, in soil or in hydroponics.

After cultivation transgenic organisms preferably transgenic plants which are used in the inventive process can be brought to the market without isolating compounds of the general formula I. Preferably the compounds of the general formula I are isolated from the organisms in the form of their free fatty acids, their lipids or oils. The purification can be done by conventional methods such as squeezing and extraction of the plants or other methods instead of the extraction such as distillation, crystallization at low temperatures, chromatography or a combination of said methods. Advantageously the plants are grinded, heated and/or vaporized before the squeezing and extraction procedure. As solvent for the extraction solvents such as hexane are used. The isolated oils are further purified by acidification with for example phosphoric acid. The free fatty acids are produced from said oils or lipids by hydrolysis. Charcoal or diatom earth are used to remove dyes from the fluid. In another preferred embodiment of the inventive process the alkyl ester of the fatty acids are produced from the oils and lipids by transesterification with an enzyme of with conventional chemistry. A preferred method is the production of the alkyl ester in the presence of alcoholates of the corresponding lower alcohols (C1 to C10 alcohols such as methanol, ethanol, propanol, butanol, hexanol etc.) such as methanolate or ethanolate. Therefore as the skilled worker knows the alcohol in the presence of a catalytic amount of a base such as NaOH or KOH is added to the oils or lipids.

In a preferred form of the inventive process the lipids can be obtained in the usual manner after the organisms have been grown. To this end, the organisms can first be harvested and then disrupted, or they can be used directly. It is advantageous to extract the lipids with suitable solvents such as a polar solvents, for example hexane, or polar solvents, for example ethanol, isopropanol, or mixtures such as hexane/isopropanol, phenol/chloroform/isoamyl alcohol, at temperatures between 0° C. and 80° C., preferably between 20° C. and 50° C. As a rule, the biomass is extracted with an excess of solvent, for example with an excess of solvent to biomass of 1:4. The solvent is subsequently removed, for example by distillation. The extraction may also be carried out with supercritical $CO_2$. After the extraction, the remainder of the biomass can be removed, for example, by filtration. Standard methods for the extraction of fatty acids from plants and microorganisms are described in Bligh et al. (Can. J. Biochem. Physiol. 37, 1959: 911-917) or Vick et al. (Plant Physiol. 69, 1982: 1103-1108).

The crude oil thus obtained can then be purified further, for example by removing cloudiness by adding polar solvents such as acetone or a polar solvents such as chloroform, followed by filtration or centrifugation. Further purification via columns or other techniques is also possible.

To obtain the free fatty acids from the triglycerides, the latter are hyrolyzed in the customary manner, for example using NaOH or KOH.

In the inventive process oils, lipids and/or free fatty acids or fractions thereof are produced. Said products can be used for the production of feed and food products, cosmetics or pharmaceuticals.

In principle all nucleic acids encoding polypeptides with Δ-8-desaturase, Δ-9-elongase and/or Δ-5-desaturase activity can be used in the inventive process. Preferably the nucleic acid sequences can be isolated for example from microorganism or plants such as fungi like *Mortierelia*, algae like *Euglena, Crypthecodinium* or *Isochrysis*, diatoms like *Phaeodactylum* or mosses like *Physcomla* or *Ceratodon*, but also non-human animals such as *Caenorhabditis* are possible as source for the nuoleic acid sequences. Advantageous nucleic acid sequences according to the invention which encode polypeptides having a Δ-8-desaturase, Δ-9-elongase and/or Δ-5-desaturase activity are originate from microorganisms or plants, advantageously *Phaeodactylum tricomutum, Ceratodon purpureus, Physcomitrella patens, Euglena gracilis* or *Isochrysis galbana. Euglena gracilis* or *Isochrysis galbana* are specific for the conversion of ω-3- or ω-6 fatty acids. Thus, the co expression of a Δ-9 elongase and a C20-specific Δ-8-desaturase leads to the formation of eicosatrienoic acid (C20:6n-3, Δ8, 11, 14) and eicosatetraenoic acid (C20:3n-4, Δ8, 11, 14, 17). Co-expression of a third gene coding for a C20-Δ5 specific desaturase leads to the production of Arachidonic acid (C20:6n-4, Δ5, 8, 11, 14) or Eicosapentaenoic acid (C20:3n-5, Δ5, 8, 11, 14, 17).

By derivative(s) of the sequences according to the invention is meant, for example, functional homologs of the polypeptides or enzymes encoded by SEQ ID NO: 2 or SEQ ID NO: 4, SEQ ID NO: 6, SEQ ID NO: 8 or SEQ ID NO: 10 which exhibit the same said specific enzymatic activity. This specific enzymatic activity allows advantageously the synthesis of unsaturated fatty acids having more than three double bonds in the fatty acid molecule. By unsaturated fatty acids is meant in what follows diunsaturated or polyunsaturated fatty acids which possess double bonds. The double bonds may be conjugated or non conjugated. The said sequences encode enzymes which exhibit Δ-9 elongase, Δ-8-desaturase or -Δ5-desaturase activity.

The enzyme according to the invention, Δ-9-elongase, Δ-8-desaturase or Δ-5-desaturase, advantageously either elongates fatty acid chains with 18 carbon atoms (see SEQ ID NO: 2) or introduces a double bond into fatty acid residues of glycerolipids, free fatty acids or acyl-CoA fatty acids at position $C_8$-$C_9$ (see SEQ ID NO: 4) or at position $C_5$-$C_6$ (see SEQ ID NO: 6, SEQ ID NO: 8 or SEQ ID NO: 10).

The nucleic acid sequence(s) according to the invention (for purposes of the application the singular encompasses the plural and vice versa) or fragments thereof may advantageously be used for isolating other genomic sequences via homology screening.

The said derivatives may be isolated, for example, from other organisms, eukaryotic organisms such as plants, especially mosses, algae, dinoflagellates or fungi, preferably algae and mosses.

Allele variants include in particular functional variants obtainable by deletion, insertion or substitution of nucleotides in the sequences depicted in SEQ ID NO: 1, SEQ ID NO: 3, SEQ ID NO: 5, SEQ ID NO: 7 or SEQ ID NO: 9 the enzymatic activity of the derived synthesized proteins being retained.

Starting from the DNA sequence described in SEQ ID NO: 1, SEQ ID NO: 3, SEQ ID NO: 5, SEQ ID NO: 7 or SEQ ID NO: 9 or parts of said sequences such DNA sequences can be isolated using, for example, normal hybridization methods or the PCR technique from other eukaryotes such as those identified above for example. These DNA sequences hybridize under standard conditions with the said sequences. For hybridization use is advantageously made of short oligonucleotides of the conserved regions of an average length of about 15 to 70 bp, preferably of about 17 to 60 bp, more preferably of about 19 to 50 bp, most preferably of about 20 to 40 bp, for example, which can be determined by comparisons with other desaturase or elongase genes in the manner known to those skilled in the art. The histidine box sequences are advantageously employed. However, longer fragments of the nucleic acids according to the invention or the complete sequences may also be used for hybridization. Depending on the nucleic acid employed: oligonucleotide, longer fragment or complete sequence, or depending on which type of nucleic acid, DNA or RNA, is used for hybridization these standard conditions vary. Thus, for example, the melting temperatures of DNA:DNA hybrids are approximately 10° C. lower than those of DNA:RNA hybrids of the same length.

By standard conditions is meant, for example, depending on the nucleic acid in question temperatures between 42° C. and 58° C. in an aqueous buffer solution having a concentration of between 0.1 and 5×SSC (1×SSC=0.15 M NaCl, 15 mM sodium citrate, pH 7.2) or additionally in the presence of 50% formamide, such as by way of example 42° C. in 5×SSC, 50% formamide. Hybridization conditions for DNA:DNA hybrids are advantageously 0.1×SSC and temperatures between approximately 20° C. and 45° C., preferably between approximately 30° C. and 45° C. For DNA:RNA hybrids the hybridization conditions are advantageously 0.1× SSC and temperatures between approximately 30° C. and 55° C., preferably between approximately 45° C. and 55° C. These specified temperatures for hybridization are melting temperature values calculated by way of example for a nucleic acid having a length of approximately 100 nucleotides and a G+C content of 50% in the absence of formamide. The experimental conditions for DNA hybridization are described in relevant genetics textbooks such as by way of example Sambrook et al., "Molecular Cloning", Cold Spring Harbor Laboratory, 1989, and may be calculated by formulae known to those skilled in the art, for example as a function of the length of the nucleic acids, the nature of the hybrids or the G+C content. Those skilled in the art may draw on the following textbooks for further information on hybridization: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology, A Practical Approach, IRL Press at Oxford University Press, Oxford.

Furthermore, by derivatives is meant homologs of the sequences SEQ ID NO: 1, SEQ ID NO: 3, SEQ ID NO: 5, SEQ ID NO: 7 and SEQ ID NO: 9, for example eukaryotic homologs, truncated sequences, single-stranded DNA of the encoding and nonencoding DNA sequence or RNA of the encoding and nonencoding DNA sequence.

In addition, by homologs of the sequences SEQ ID NO: 1, SEQ ID NO: 3, SEQ ID NO: 5, SEQ ID NO: 7 and SEQ ID NO: 9 is meant derivatives such as by way of example promoter variants. These variants may be modified by one or more nucleotide exchanges, by insertion(s) and/or deletion(s) without, however, adversely affecting the functionality or efficiency of the promoters. Furthermore, the promoters can have their efficiency increased by altering their sequence or be completely replaced by more effective promoters even of foreign organisms.

By derivatives is also advantageously meant variants whose nucleotide sequence has been altered in the region from −1 to −2000 ahead of the start codon in such a way that the gene expression and/or the protein expression is modified, preferably increased. Furthermore, by derivatives is also meant variants which have been modified at the 3' end.

The nucleic acid sequences according to the invention which encode a Δ-8-desaturase, a Δ-5-desaturase and/or a Δ-9-elongase may be produced by synthesis or obtained naturally or contain a mixture of synthetic and natural DNA components as well as consist of various heterologous Δ-8-desaturase, Δ-5-desaturase and/or Δ-9-elongase gene segments from different organisms. In general, synthetic nucleotide sequences are produced with codons which are preferred by the corresponding host organisms, plants for example. This usually results in optimum expression of the heterologous gene. These codons preferred by plants may be determined from codons having the highest protein frequency which are expressed in most of the plant species of interest. An example concerning *Corynebacterium glutamicum* is provided in Wada et al. (1992) *Nucleic Acids Res.* 20:2111-2118). Such experiments can be carried out using standard methods and are known to the person skilled in the art.

Functionally equivalent sequences which encode the Δ-8-desaturase, Δ-5-desaturase and/or Δ-9-elongase gene are those derivatives of the sequence according to the invention which despite differing nucleotide sequence still possess the desired functions, that is to say the enzymatic activity and specific selectivity of the proteins. Thus, functional equivalents include naturally occurring variants of the sequences described herein as well as artificial ones, e.g. artificial nucleotide sequences adapted to the codon use of a plant which have been obtained by chemical synthesis.

In addition, artificial DNA sequences are suitable, provided, as described above, they mediate the desired property, for example an increase in the content of Δ-8 and/or Δ-5 double bonds in fatty acids, oils or lipids in organisms such as in a plant by over-expression of the Δ-8- and/or Δ-5-desaturase gene in preferably in crop plants. Such artificial DNA sequences can exhibit Δ-8 and/or Δ-5-desaturase and/or Δ-9-elongase activity, for example by back-translation of proteins constructed by means of molecular modeling, or be determined by in vitro selection. Possible techniques for in vitro evolution of DNA to modify or improve the DNA sequences are described in Patten, P. A. et al., Current Opinion in Biotechnology 8, 724-733(1997) or in Moore, J. C. et al., Journal of Molecular Biology 272, 336-347 (1997). Particularly suitable are encoding DNA sequences which are obtained by back-translation of a polypeptide sequence in accordance with the codon use specific to the host plant. Those skilled in the art familiar with the methods of plant genetics can easily determine the specific codon use by computer analyses of other known genes of the plant to be transformed.

Other suitable equivalent nucleic acid sequences which may be mentioned are sequences that encode fusion proteins, a component of the fusion protein being a Δ-8- and/or a Δ-5-desaturase polypeptide and/or a Δ-9 elongase polypeptide or a functionally equivalent part thereof. The second part of the fusion protein can be, for example, another polypeptide having enzymatic activity or an antigenic polypeptide sequence by means of which it is possible to demonstrate Δ-8- and/or Δ-5-desaturase or Δ-9-elongase expression (e.g. myc tag or his tag). Preferably, however, this is a regulatory protein sequence, such as by way of example a signal sequence for the endoplasmic reticulum (=ER) which directs the Δ-8- and/or Δ-5-desaturase protein and/or the Δ-9-elongase protein to the desired point of action, or regulatory sequences which influence the expression of the nucleic acid sequence according to the invention, such as promoters or terminators. In another preferred embodiment the second part of the fusion protein is a plastidial targeting sequence as described by Napier J. A. [Targeting of foreign proteins to the chloroplast, Methods Mol. Biol., 49, 1995: 369-376]. A preferred used vector comprising said plastidial targeting sequence is disclosed by Colin Lazarus [Guerineau F., Woolston S., Brooks L., Mullineaux P. "An expression cassette for targeting foreign proteins into chloroplast; Nucleic. Acids Res., Dec. 9, 16 (23), 1988: 11380].

Advantageously, the Δ-8-desaturase and Δ-9-elongase and/or the Δ-5-desaturase genes in the method according to the invention may be combined with other genes for fatty acid biosynthesis. Examples of such genes are the acyl transferases, other desaturases or elongases such as Δ-4-, Δ-5- or Δ-6-desaturases or ω-3- and/or (specific desaturases such as Δ-12 (for $C_{18}$ fatty acids), Δ-15 (for $C_{18}$ fatty acids) or Δ-19 (for $C_{22}$ fatty acids) and/or such as Δ-5- or Δ-6-elongases. For in vivo and especially in vitro synthesis combination with e.g.

NADH cytochrome B5 reductases which can take up or release reduction equivalents is advantageous.

By the amino acid sequences according to the invention is meant proteins which contain an amino acid sequence depicted in the sequences SEQ ID NO: 2, SEQ ID NO: 4, SEQ ID NO: 6, SEQ ID NO: 8 and SEQ ID NO: 10 or a sequence obtainable therefrom by substitution, inversion, insertion or deletion of one or more amino acid groups (such sequences are derivatives of SEQ ID NO: 2, SEQ ID NO: 4, SEQ ID NO: 6, SEQ ID NO: 8 and/or SEQ ID NO: 10), whereas the enzymatic activities of the proteins depicted in SEQ ID NO: 2, SEQ ID NO: 4, SEQ ID NO: 6, SEQ ID NO: 8 and SEQ ID NO: 10 being retained or not substantially reduced, that is they still possess the same enzymatic specificity. By "not substantially reduced" or "the same enzymatic activity" is meant all enzymes which still exhibit at least 10%, preferably 20%, particularly preferably 30%, of the enzymatic activity of the initial enzyme obtained from the wild type source organism such as organisms of the genus *Physcomitrella, Ceratodon, Borago, Thraustochytrium, Schizochytrium, Phytophtora, Mortierella, Caenorhabditis, Aleuriba, Muscariodides, Isochrysis, Phaeodactylum, Crypthecodinium* or *Euglenia* preferred source organisms are organisms such as the species *Euglenia gracilis, Isochrysis galbana, Phaeodactylum tricomutum, Caenorhabditis elegans, Thraustochytrium, Phytophtora infestans, Ceratodon purpureus, Isochrysis galbana, Aleuritia farinosa, Muscariodides vialii, Mortierella alpina, Borago officinalis or Physcomitrella* patens. For the estimation of an enzymatic activity which is "not substantially reduced" or which has the "same enzymatic activity" the enzymatic activity of the derived sequences are determined and compared with the wild type enzyme activities. In doing this, for example, certain amino acids may be replaced by others having similar physiochemical properties (space filling, basicity, hydrophobicity, etc.). For example, arginine residues are exchanged for lysine residues, valine residues for isoleucine residues or aspartic acid residues for glutamic acid residues. However, one or more amino acids may also be swapped in sequence, added or removed, or a plurality of these measures may be combined with one another.

By derivatives is also meant functional equivalents which in particular also contain natural or artificial mutations of an originally isolated sequence encoding Δ-8-desaturase, a Δ-9-elongase and/or a Δ-5-desaturase which continue to exhibit the desired function, that is the enzymatic activity and substrate selectivity thereof is not substantially reduced. Mutations comprise substitutions, additions, deletions, exchanges or insertions of one or more nucleotide residues. Thus, for example, the present invention also encompasses those nucleotide sequences which are obtained by modification of the Δ-8-desaturase nucleotide sequence, the Δ-5-desaturase nucleotide sequence and/or the Δ-9-elongase nucleotide sequence used in the inventive processes. The aim of such a modification may be, e.g., to further bound the encoding sequence contained therein or also, e.g., to insert further restriction enzyme interfaces.

Functional equivalents also include those variants whose function by comparison as described above with the initial gene or gene fragment is weakened (=not substantially reduced) or reinforced (=enzyme activity higher than the activity of the initial enzyme, that is activity is higher than 100%, preferably higher than 110%, particularly preferably higher than 130%).

At the same time the nucleic acid sequence may, for example, advantageously be a DNA or cDNA sequence. Suitable encoding sequences for insertion into an expression cassette according to the invention include by way of example those which encode a Δ-8-desaturase, a Δ-5-desaturase and/or a Δ-9-elongase with the sequences described above and lend the host the ability to overproduce fatty acids, oils or lipids having double bonds in the Δ-8-position and Δ-5-position, it being advantageous when at the same time fatty acids having at least four double bonds are produced. These sequences may be of homologous or heterologous origin.

By the expression cassette (=nucleic acid construct or fragment or gene construct) according to the invention is meant the sequences specified in SEQ ID NO: 1, SEQ ID NO: 3, SEQ ID NO: 5, SEQ ID NO: 7 and/or SEQ ID NO: 9 which result from the genetic code and/or derivatives thereof which are functionally linked with one or more regulation signals advantageously to increase the gene expression and which control the expression of the encoding sequence in the host cell. These regulatory sequences should allow the selective expression of the genes and the protein expression. Depending on the host organism this may mean, for example, that the gene is expressed and/or overexpressed only after induction or that d is expressed and/or overexpressed immediately. Examples of these regulatory sequences are sequences to which inductors or repressors bind and in this way regulate the expression of the nucleic acid. In addition to these new regulation sequences or instead of these sequences the natural regulation of these sequences ahead of the actual structural genes may still be present and optionally have been genetically modified so that natural regulation was switched off and the expression of the genes increased. However, the gene construct can also be built up more simply, that is no additional regulation signals have been inserted ahead of the nucleic acid sequence or derivatives thereof and the natural promoter with its regulation has not been removed. Instead of this the natural regulation sequence was mutated in such a way that no further regulation ensues and/or the gene expression is heightened. These modified promoters in the form of part sequences (=promoter containing parts of the nucleic acid sequences according to the invention) can also be brought on their own ahead of the natural gene to increase the activity. In addition, the gene construct may advantageously also contain one or more so-called enhancer sequences functionally linked to the promoter which allow enhanced expression of the nucleic acid sequence. At the 3' end of the DNA sequences additional advantageous sequences may also be inserted, such as further regulatory elements or terminators. The Δ-8- and/or Δ-5-desaturase gene and/or the Δ-9-elongase gene may be present in one or more copies in the expression cassette (=gene construct).

As described above, the regulatory sequences or factors can preferably positively influence and so increase the gene expression of the introduced genes. Thus, reinforcement of the regulatory elements advantageously on the transcription level may be effected by using powerful transcription signals such as promoters and/or enhancers. However, in addition reinforcement of translation is also possible, for example by improving the stability of the mRNA.

Suitable promoters in the expression cassette are in principle all promoters which can control the expression of foreign genes in organisms such as microorganisms like protozoa such as ciliates, algae such as green, brown, red or blue algae such as *Euglenia*, bacteria such as gram-positive or gram-negative bacteria, yeasts such as *Saccharomyces, Pichia* or *Schizosaccharomyces* or fungi such as *Mortierella, Thraustochytrium* or *Schizochytium* or plants such as *Aleuritia*, advantageously in plants or fungi. Use is preferably made in particular of plant promoters or promoters derived from a plant virus. Advantageous regulation sequences for the method according to the invention are found for example in promoters such as cos, tac, trp, tet, trp-tet, Ipp, Iac, Ipp-Iac, IacI$^{q-}$, T7, T5, T3, gal, trc, ara, SP6, λ-P$_R$ or in λ-P$_L$ promoters which are employed advantageously in gram-negative bacteria. Other advantageous regulation sequences are found, for example, in the gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21(1980) 285-294], SSU, OCS, lib4, STLS1, B33, nos (=Nopalin Synthase Promoter) or in the ubiquintin or phaseolin promoter. The expression cassette may also contain a chemically inducible promoter by means of which the expression of the exogenous Δ-8- and/or Δ-5-desaturase gene and/or the Δ-9-elongase gene in the organisms can be controlled advantageously in the plants at a particular time. Advantageous plant promoters of this type are by way of example the PRP1 promoter [Ward et al., Plant. Mol. Biol. 22(1993), 361-366], a promoter inducible by benzenesulfonamide (BP 388 186), a promoter inducible by tetracydine [Gatz et al., (1992) Plant J. 2,397-404], a promoter inducible by salicylic acid (WO 95/19443), a promoter inducible by abscissa acid (EP 335 528) and a promoter inducible by ethanol or cyclohexanone (WO93/21334). Other examples of plant promoters which can advantageously be used are the promoter of cytosolic FBPase from potato, the ST-LSI promoter from potato (Stockhaus et al., EMBO J. 8 (1989) 2445245), the promoter of phosphoribosyl pyrophosphate amido transferase from Glycine max (see also gene bank accession number U87999) or a no diene-specific promoter as described in EP 249 676. Particularly advantageous are those plant promoters which ensure expression in tissues or plant parts/organs in which fatty acid biosynthesis or the precursor stages thereof occurs, as in endosperm or in the developing embryo for example. Particularly noteworthy are advantageous promoters which ensure seed-specific expression such as by way of example the USP promoter or derivatives thereof, the LEB4 promoter, the phaseolin promoter or the napin promoter. The particularly advantageous USP promoter cited according to the invention or its derivatives mediate very early gene expression in seed development [Baeumlein et al., Mol Gen Genet, 1991, 225 (3): 459-67]. Other advantageous seed-specific promoters which may be used for monocotylodonous or dicotylodonous plants are the promoters suitable for dicotylodons such as napin gene promoters, likewise cited by way of example, from oilseed rape (U.S. Pat. No. 5,608,152), the oleosin promoter from *Arabidopsis* (WO 98/45461), the phaseolin promoter from *Phaseolus vulgaris* (U.S. Pat. No. 5,504,200), the Bce4 promoter from Brassica (WO 91/13980) or the leguminous B4 promoter (LeB4, Baeumlein et al., Plant J., 2, 2, 1992: 233-239) or promoters suitable for monocotylodons such as the promoters of the Ipt2 or *Ipt*1 gene in barley (WO 95/15389 and WO 95/23230) or the promoters of the barley hordeine gene, the rice glutelin gene, the rice oryzin gene, the rice prolamin gene, the wheat gliadin gene, the white glutelin gene, the corn zein gene, the oats glutelin gene, the sorghum kasirin gene or the rye secalin gene which are described in WO99/16890.

Furthermore, particularly preferred are those promoters which ensure the expression in tissues or plant parts in which, for example, the biosynthesis of fatty acids, oils and lipids or the precursor stages thereof takes place. Particularly noteworthy are promoters which ensure a seed-specific expression. Noteworthy are the promoter of the napin gene from oilseed rape (U.S. Pat. No. 5,608,152), the USP promoter from *Vicia faba* (USP=unknown seed protein, Baeumlein et al., Mol Gen Genet, 1991, 225 (3): 459-67), the promoter of the oleosin gene from *Arabidopsis* (WO98/45461), the phaseolin promoter (U.S. Pat. No. 5,504,200) or the promoter of the legumin B4 gene (LeB4; Baeumlein et al., 1992, Plant Journal, 2 (2): 233-9). Other promoters to be mentioned are that of the Ipt2 or Ipt1 gene from barley (WO95/15389 and WO95/23230) which mediate seed-specific expression in monocotyledonous plants. Other advantageous seed specific promoters are promoters such as the promoters from rice, corn or wheat disclosed in WO 99/16890 or Amy32b, Amy6-6 or aleurain (U.S. Pat. No. 5,677,474), Bce4 (rape, U.S. Pat. No. 5,530, 149), glycine (soy bean, EP 571 741), phosphoenol pyruvat carboxylase (soy bean, JP 06/62870), ADR12-2 (soy bean, WO 98/08962), isocitratlyase (rape, U.S. Pat. No. 5,689,040) or β-amylase (barley, EP 781 849).

As described above, the expression construct (=gene construct, nucleic acid construct) may contain yet other genes which are to be introduced into the organisms. These genes can be subject to separate regulation or be subject to the same regulation region as the Δ-8- and/or Δ-5-desaturase gene and/ or the Δ-9-elongase gene. These genes are by way of example other biosynthesis genes, advantageously for fatty acid biosynthesis, which allow increased synthesis. Examples which may be mentioned are the genes for Δ-15-, Δ-12-, Δ-9-, Δ-5-, Δ-4-desaturase, α-ketoacyl reductases, α-ketoacyl synthases, elongases or the various hydroxylases and acy-ACP thioesterases. The desaturase genes are advantageously used in the nucleic acid construct.

In principle all natural promoters with their regulation sequences can be used like those named above for the expression cassette according to the invention and the method according to the invention. Over and above this, synthetic promoters may also advantageously be used.

In the preparation of an expression cassette various DNA fragments can be manipulated in order to obtain a nucleotide sequence which usefully reads in the correct direction and is equipped with a correct reading raster. To connect the DNA fragments (=nucleic acids according to the invention) to one another adaptors or linkers may be attached to the fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which encodes a Δ-8-desaturase gene, a Δ-5-desaturase gene and/or a Δ-9-elongase gene and a region for transcription termination. Different termination regions can be exchanged for one another in any desired fashion.

Furthermore, manipulations which provide suitable restriction interfaces or which remove excess DNA or restriction interfaces can be employed. Where insertions, deletions or substitutions, such as transitions and transversions, come into consideration, in vitro mutagenesis, primer repair, restriction or ligation may be used. In suitable manipulations such as restriction, cheving back or filling of overhangs for blunt ends complementary ends of the fragments can be provided for the ligation.

For an advantageous high expression the attachment of the specific ER retention signal SEKDEL inter alia can be of importance (Schouten, A et al., Plant Mol. Biol. 30 (1996), 781-792). In this way the average expression level is tripled or even quadruped. Other retention signals which occur naturally in plant and animal proteins located in the ER may also be employed for the construction of the cassette. In another preferred embodiment a plastidial targeting sequence is used as described by Napier J. A. [Targeting of foreign proteins to the chloroplast, Methods Mol. Biol., 49, 1995: 369-376]. A preferred used vector comprising said plastidial targeting sequence is disclosed by Colin Lazarus [Guerineau F., Woolston S., Brooks L, Mullineaux P. "An expression cassette for targeting foreign proteins into chloroplast; Nucleic. Acids Res., Dec. 9, 16 (23), 1988: 11380].

Preferred polyadenylation signals are plant polyadenylation signals, preferably those which substantially correspond to T-DNA polyadenylation signals from *Agrobacterium tumefaciens*, in particular gene 3 of the T-DNA (octopin synthase) of the Ti plasmid pTiACH5 (Gielen et al., EMBO J. 3 (1984), 835 et seq.) or corresponding functional equivalents.

An expression cassette is produced by fusion of a suitable promoter with a suitable Δ-8- and/or Δ-5-desaturase DNA sequence and/or a suitable Δ-9-elongase DNA sequence together with a polyadenylation signal by common recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

In the preparation of an expression cassette various DNA fragments can be manipulated to produce a nucleotide sequence which usefully reads in the correct direction and is equipped with a correct reading raster. Adapters or linkers can be attached to the fragments for joining the DNA fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant In the 5'-3' transcription direction the expression cassette contains the promoter, a DNA sequence which either encodes a Δ-8- and/or Δ-5-desaturase gene and/or a Δ-9-elongase gene and a region for transcription termination. Different termination regions can be exchanged for one another in any desired fashion.

In the preparation of an expression cassette various DNA fragments can be manipulated to produce a nucleotide sequence which usefully reads in the correct direction and is equipped with a correct reading raster. Adapters or linkers can be attached to the fragments for joining the DNA fragments.

The DNA sequences encoding the nucleic acid sequences used in the inventive processes such as the Δ-8-desaturase from *Euglena gracilis*, the Δ-9-elongase from *Isochrysis galbana* and/or the Δ-5-desaturase for example from *Caenorhabditis elegans, Mortierella alpina, Borage officinalis* or *Physcomitrella patens* contain all the sequence characteristics needed to achieve correct localization of the site of fatty acid, lipid or oil biosynthesis. Accordingly, no further targeting sequences are needed per se. However, such a localization may be desirable and advantageous and hence artificially modified or reinforced so that such fusion constructs are also a preferred advantageous embodiment of the invention.

Particularly preferred are sequences which ensure targeting in plastids. Under certain circumstances targeting into other compartments (reported in: Kermode, Crit. Rev. Plant Sci. 15, 4 (1996), 285-423) may also be desirable, e.g. into vacuoles, the mitochondrium, the endoplasmic reticulum (ER), peroxisomes, lipid structures or due to lack of corresponding operative sequences retention in the compartment of origin, the cytosol.

Advantageously, the nucleic acid sequences according to the invention or the gene construct together with at least one reporter gene are cloned into an expression cassette which is introduced into the organism via a vector or directly into the genome. This reporter gene should allow easy detection via a growth, fluorescence, chemical, bioluminescence or resistance assay or via a photometric measurement. Examples of reporter genes which may be mentioned are antibiotic- or herbicide-resistance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphobansferase gene or the BASTA (=gluphosinate-resistance) gene. These genes permit easy measurement and quantification of the transcription activity and hence of the expression of the genes. In this way genome positions may be identified which exhibit differing productivity.

In a preferred embodiment an expression cassette comprises upstream, i.e. at the 5' end of the encoding sequence, a promoter and downstream, i.e. at the 3' end, a polyadenylation signal and optionally other regulatory elements which are operably linked to the intervening encoding sequence for Δ-8-desaturase, Δ-9-elongase and/or Δ-5-desaturase DNA sequence. By an operable linkage is meant the sequential arrangement of promoter, encoding sequence, terminator and optionally other regulatory elements in such a way that each of the regulatory elements can fulfill its function in the expression of the encoding sequence in due manner. The sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 (1987), 8693-8711).

An expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a prokaryotic or eukaryotic host organism, for example a microorganism such as a fungus or a plant the expression cassette is advantageously inserted into a vector such as by way of example a plasmid, a phage or other DNA which allows optimum expression of the genes in the host organism. Examples of suitable plasmids are: in *E. coli* pLG338, pACYC184, pBR series such as e.g. pBR322, pUC series such as pUC18 or pUC19, M113mp series, pKC30, pRep4, pHS1, pHS2, pPLc236, pMBL24, pLG200, pUR290, pIN-III[113]-B1, λgt11 or pBdCl; in Streptomyoes pIJ101, pIJ364, pIJ702 or pIJ361; in Bacillus pUB110, pC194 or pBD214; in *Corynebacterium* pSA77 or pAJ667; in fungi pALS1, pIL2 or pBB116; other advantageous fungal vectors are described by Romanos, M. A. et al, [(1992) "Foreign gene expression in yeast a review", *Yeast* 8: 423488] and by van den Hondel, C. A. M. J. J. et al. [(1991) "Heterologous gene expression in filamentous fungi" as well as in More Gene Manipulations in Fungi [J. W. Bennet & L. L. Lasure, eds., pp. 396-428: Academic Press: San Diego] and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 µM, pAG-1, YEp6, YEp13 or pEMBLYe23. Examples of algal or plant promoters are pLGV23, pGHIac+, pBIN19, pAK2004, pVKH or pDH51 (see Schmidt, R. and Willmitzer, L., 1988). The vectors identified above or derivatives of the vectors identified above are a small selection of the possible plasmids. Further plasmids are well known to those skilled in the art and may be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Ch. 6/7, pp. 71-119. Advantageous vectors are known as shuttle vectors or binary vectors which replicate in *E. coli* and *Agrobacterium*.

By vectors is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

In a further advantageous embodiment the nucleic acid sequence according to the invention can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

By way of example the plant expression cassette can be installed in the pRT transformation vector ((a) Toepfer et al., 1993, Methods Enzymol., 217: 66-78; (b) Toepfer et al. 1987, Nucl. Acids. Res. 15: 5890 ff.).

Alternatively, a recombinant vector (=expression vector) can also be transcribed and translated in vitro, e.g. by using the T7 promoter and the T7 RNA polymerase.

Expression vectors employed in prokaryotes frequently make use of inducible systems with and without fusion proteins or fusion oligopeptides, wherein these fusions can ensue in both N-terminal and C-terminal manner or in other useful domains of a protein. Such fusion vectors usually have the following purposes: i.) to increase the RNA expression rate; ii.) to increase the achievable protein synthesis rate; iii.) to increase the solubility of the protein; iv.) or to simplify purification by means of a binding sequence usable for affinity chromatography. Proteolytic cleavage points are also frequently introduced via fusion proteins which allows cleavage of a portion of the fusion protein and purification. Such recognition sequences for proteases are recognized, e.g. factor Xa, thrombin and enterokinase.

Typical advantageous fusion and expression vectors are PGEX [Pharmacia Biotech Inc; Smith, D. B. and Johnson, K. S. (1988) *Gene* 67: 31-40], pMAL (New England Biolabs, Beverly, Mass.) and pRIT5 (Pharmacia, Piscataway, N.J.) which contains glutathione S-transferase (GST), maltose binding protein or protein A.

Other examples of *E. coli* expression vectors are pTrc [Amann et al., (1988) *Gene* 69:301-315] and pET vectors [Studier et al., Gene Expression Technology: Methods in Enzymology 185, Academic Press, San Diego, Calif. (1990) 60-89; Stratagene, Amsterdam, The Netherlands].

Other advantageous vectors for use in yeast are pYepSec1 (Baldari, et al., (1987) *Embo J.* 6:229-234), pMFa (Kudian and Herskowitz, (1982) *Cell* 30:933-943), pJRY88 (Schultz et al., (1987) *Gene* 54:113-123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., pp. 1-28, Cambridge University Press: Cambridge.

Alternatively, insect cell expression vectors can also be advantageously utilized, e.g. for expression in Sf 9 cells. These are e.g. the vectors of the pAc series (Smith et al. (1983) *Mol. Cell Biol.* 3:2156-2165) and the pVL series (Lucklow and Summers (1989) *Virology* 170:31-39).

Furthermore, plant cells or algal cells can advantageously be used for gene expression. Examples of plant expression vectors may be found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", *Nucl. Acid. Res.* 12: 8711-8721.

Furthermore, the nucleic acid sequences may also be expressed in mammalian cells, advantageously in nonhuman mammalian cells. Examples of corresponding expression vectors are pCDM8 and pMT2PC referred to in: Seed, B. (1987) *Nature* 329:840 or Kaufman et al. (1987) *EMBO J.* 6: 187-195). At the same time promoters preferred for use are of viral origin, such as by way of example promoters of polyoma, adenovirus 2, cytomegalovirus or simian virus 40. Other prokaryotic and eukaryotic expression systems are referred to in chapters 16 and 17 of Sambrook et al., *Molecular Cloning: A Laboratory Manual.* 2nd, ed., Cold Spring Harbor Laboratory, Cold Spring Harbor Laboratory Press, Cold Spring Harbor, N.Y., 1989.

The host organism (=transgenic organism) advantageously contains at least one copy of the nucleic acid according to the invention and/or of the nucleic acid construct according to the invention.

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

In the case of microorganisms, those skilled in the art can find appropriate methods in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et. al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol) induced DNA uptake, the "biolistic" method using the gene cannon—referred to as the particle bombardment method, electroporation, the incubation of dry embryos in DNA solution, microinjection and gene transfer mediated by Agrobacterium. Said methods are described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of Agrobacterium tumefaciens is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

*Agrobacteria* transformed by an expression vector according to the invention may likewise be used in known manner for the transformation of plants such as test plants like Arabidopsis or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, tagetes, alfalfa, lettuce and the various tree, nut and vine species, in particular of oil-containing crop plants such as soybean, peanut, castor oil plant, sunflower, corn, cotton, flax, oilseed rape, coconut, oil palm, safflower (*Cartharus tinctorius*) or cocoa bean, e.g. by bathing bruised leaves or chopped leaves in an agrobacterial solution and then culturing them in suitable media. For the production of PUFAs, for example stearidonic acid, eicosapentaenoic acid and docosahexaenoic acid, borage, linseed, sunflower, safflower or Primulaceae are advantageously suitable. Other suitable organisms for the production of for example γ-linoleic acid, dihomo-γ-linoleic acid or arachidonic acid are for example linseed, sunflower or safflower.

The genetically modified plant cells may be regenerated by all of the methods known to those skilled in the art. Appropriate methods can be found in the publications referred to above by S. D. Kung and R. Wu, Potrykus or Höfgen and Wilimitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms. The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

For the purposes of the invention "transgenic" or "recombinant" means with regard for example to a nucleic acid sequence, an expression cassette (=gene construct, nucleic acid construct) or a vector containing the nucleic acid sequence according to the invention or an organism transformed by the nucleic acid sequences, expression cassette or vector according to the invention all those constructions produced by genetic engineering methods in which either a) the nucleic acid sequence depicted in SEQ ID NO: 1, SEQ ID NO: 3, SEQ ID NO: 5, SEQ ID NO: 7, SEQ ID NO: 9 or its derivatives or parts thereof or b) a genetic control sequence functionally linked to the nucleic acid sequence described under (a), for example a 3'- and/or 5'-genetic control sequence such as a promoter or terminator, or c) (a) and (b)

are not found in their natural, genetic environment or have been modified by genetic engineering methods, wherein the modification may by way of example be a substitution, addition, deletion, inversion or insertion of one or more nucleotide residues. Natural genetic environment means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding Δ-8-desaturase, Δ-9-elongase and/or Δ-5-desaturase gene—turns into a transgenic expression cassette when the latter is modified by unnatural, synthetic ("artificial") methods such as by way of example a mutagenesis. Appropriate methods are described by way of example in U.S. Pat. No. 5,565,350 or WO 00/15815.

Suitable organisms or host organisms for the nucleic acid, expression cassette or vector according to the invention are advantageously in principle all organisms which are able to synthesize fatty acids, especially unsaturated fatty acids or are suitable for the expression of recombinant genes as described above. Further examples which may be mentioned are plants such as *Arabidopsis*, *Asteraceae* such as *Calendula* or crop plants such as soybean, peanut, castor oil plant, sunflower, corn, cotton, flax, oilseed rape, coconut, oil palm, safflower (*Carthamus tinctorius*) or cocoa bean, microorganisms such as fungi, for example the genus *Mortierella*, *Saprolegnia* or *Pythium*, bacteria such as the genus *Escherichia*, yeasts such as the genus *Saccharomyces*, cyanobacteria, ciliates, algae or protozoa such as dinoflagellates like *Crypthecodinium*. Preference is given to organisms which can naturally synthesize oils in relatively large quantities such as fungi like *Mortierella alpina*, *Pythium insidiosum* or plants such as soybean, oilseed rape, coconut, oil palm, safflower, flax, castor oil plant, *Calendula*, peanut, cocoa bean or sunflower, or yeasts such as *Saccharomyces cerevisiae* and particular preference is given to soybean, flax, oilseed rape, sunflower, *Calendula, Mortierella* or *Saccharomyces cerevisiae*. In principle, apart from the transgenic organisms identified above, transgenic animals, advantageously nonhuman animals, are suitable, for example *C. elegans.*

Further useful host cells are identified in: Goeddel, *Gene Expression Technology: Methods in Enzymology* 185, Academic Press, San Diego, Calif. (1990).

Usable expression strains, e.g. those exhibiting a relatively low protease activity, are described in: Gottesman, S., *Gene Expression Technology: Methods in Enzymology* 185, Academic Press, San Diego, Calif. (1990) 119-128.

A further object of the invention relates to the use of an expression cassette containing DNA sequences encoding a Δ-8-desaturase, a Δ-9-elongase and/or a Δ-5-desaturase gene or DNA sequences hybridizing there with for the transformation of plant cells, tissues or parts of plants. The aim of use is to increase the content of fatty acids, oils or lipids having an increased content of double bonds.

In doing so, depending on the choice of promoter, the Δ-8-desaturase, a Δ-9-elongase and/or a Δ-5-desaturase gene can be expressed specifically in the leaves, in the seeds, the nodules, in roots, in the stem or other parts of the plant Those transgenic plants overproducing fatty acids, oils or lipids having at least three double bonds in the fatty acid molecule, the reproductive material thereof, together with the plant cells, tissues or parts thereof are a further object of the present invention.

The expression cassette or the nucleic acid sequences according to the invention containing a Δ-8-desaturase, a Δ-9-elongase and/or a Δ-5-desaturase gene sequence can, moreover, also be employed for the transformation of the organisms identified by way of example above such as bacteria, cyanobacteria, yeasts, filamentous fungi, ciliates and algae with the objective of increasing the content of fatty acids, oils or lipids possessing at least three double bonds.

Within the framework of the present invention, increasing the content of fatty acids, oils or lipids possessing at least three double bonds means, for example, the artificially acquired trait of increased biosynthetic performance due to functional overexpression of the Δ-8-desaturase, Δ-9-elongase and/or Δ-5-desaturase gene in the organisms according to the invention, advantageously in the transgenic plants according to the invention, by comparison with the nongenetically modified initial plants at least for the duration of at least one plant generation.

The preferred locus of biosynthesis, of fatty acids, oils or lipids for example, is generally the seed or cell layers of the seed so that a seed-specific expression of the Δ-8-desaturase, Δ-9-elongase and/or Δ-5-desaturase gene is appropriate. It is, however, obvious that the biosynthesis of fatty acids, oils or lipids need not be limited to the seed tissue but rather can also occur in tissue-specific manner in all other parts of the plant— in epidermis cells or in the nodules for example.

A constitutive expression of the exogenous Δ-8-desaturase, Δ-9-elongase and/or Δ-5-desaturase gene is, moreover, advantageous. On the other hand, however, an inducible expression may also appear desirable.

The efficiency of the expression of the Δ-8-desaturase, Δ-9-elongase and/or Δ-5-desaturase gene can be determined, for example, in vito by shoot meristem propagation. In addition, an expression of the Δ-8-desaturase, Δ-9-elongase and/ or Δ-5-desaturase gene modified in nature and level and its effect on fatty acid, oil or lipid biosynthesis performance can be tested on test plants in greenhouse trials.

An additional object of the invention comprises transgenic organisms such as transgenic plants transformed by an expression cassette containing a Δ-8-desaturase, a Δ-9-elongase and/or a Δ-5-desaturase gene sequence according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, tapioca, cassava, arrowroot, alfalfa, lettuce and the various tree, nut and vine species.

For the purposes of the invention plants are mono- and dicotyledonous plants, mosses or algae.

A further refinement according to the invention are transgenic plants as described above which contain a nucleic acid sequence according to the invention or a expression cassette according to the invention.

Other objects of the invention are:

A method for the transformation of a plant comprising the introduction of expression cassettes according to the invention containing a Δ-8-desaturase, a Δ-9-elongase and/or a Δ-5-desaturase gene sequence derived from algae such as *Euglenia* or *Isochrysis*, fungi such as *Mortierella* or mosses such as *Physcomitrella* or DNA' sequences hybridizing therewith into a plant cell, into callus tissue, an entire plant or protoplasts of plants.

A method for producing PUFAs, wherein the method comprises the growing of a transgenic organism comprising a nucleic acid as des herein or a vector encoding a Δ-8-desaturase, a Δ-9-elongase and/or a Δ-5-desaturase which specifically synthesize poly unsaturated fatty acids with at least three double bonds in the fatty acid molecule Use of a Δ-8-desaturase, a Δ-9-elongase and/or a Δ-5-desaturase DNA gene sequence or DNA sequences hybridizing therewith for the production of plants having an increased content of fatty acids, oils or lipids having at least three double bonds due to the expression of said Δ-8-desaturase, Δ-9-elongase and/or Δ-5-desaturase DNA sequence in plants.

Proteins containing the amino acid sequences depicted in SEQ ID NO: 2, SEQ ID NO: 8 or its derivatives.

Use of said proteins having the sequences SEQ ID NO: 2 or SEQ ID NO: 8 for producing unsaturated fatty acids.

A further object according to the invention is a method for producing unsaturated fatty acids comprising: introducing at least one said nucleic acid sequence described herein or at least one nucleic acid construct or vector containing said nucleic acid sequence into a preferably oil-producing organism such as a plant or a fungi; growing said organism; isolating oil contained in said organism; and liberating the fatty acids present in said oil. These unsaturated fatty acids advantageously contain at least three double bonds in the fatty acid molecule. The fatty acids may be liberated from the oils or lipids, for example by basic hydrolysis, e.g. using NaOH or KOH or by acid hydrolysis preferably in the presence of an alcohol such as methanol or ethanol. Said fatty acid liberation leads to free fatty acids or to the corresponding alkyl esters of the fatty acids. In principle an enzymatic hydrolysis for example with a lipase as enzyme is also possible. Starting from said free fatty acids or fatty acid alkyl esters mono-, di- and/or triglycerides can be synthesized either chemically or enzymatically. In another preferred embodiment of the inventive process the alkyl ester of the fatty acids are produced from the oils and lipids by transesterification with an enzyme of with conventional chemistry. A preferred method is the production of the alkyl ester in the presence of alcoholates of the corresponding lower alcohols (C1 to C10 alcohols such as methanol, ethanol, propanol, butanol, hexanol etc.) such as methanolate or ethanolate. Therefore as the skilled worker knows the alcohol in the presence of a catalytic amount of a base such as NaOH or KOH is added to the oils or lipids.

A method for producing triglycerides having an increased content of unsaturated fatty acids comprising: introducing at least one said nucleic acid sequence according to the invention or at least one expression cassette according to the invention into an oilproducing organism; growing said organism; and isolating oil contained in said organism; is also numbered among the objects of the invention.

A further object according to the invention is a method for producing triglycerides having an increased content of unsaturated fatty acids by incubating triglycerides containing saturated or unsaturated or saturated and unsaturated fatty acids with at least one of the proteins encoded by the sequences SEQ ID NO: 2, SEQ ID NO: 4, SEQ ID NO: 6, SEQ ID NO: 8 or SEQ ID NO: 10. The method is advantageously carried out in the presence of compounds which can take up or release reduction equivalents. The fatty acids can then be liberated from the triglycerides.

A further object according to the invention of said method for producing triglycerides having an increased content of unsaturated fatty acids advantageously having an increased content of unsaturated fatty acids is a method wherein the fatty acids are liberated from the triglycerides with the aid of basic hydrolysis known to those skilled in the art or by means of an enzyme such as a lipase.

The methods specified above advantageously allow the synthesis of fatty acids or triglycerides having an increased content of fatty acids containing at least three double bonds in the fatty acid molecule.

The methods identified above advantageously allow the synthesis of fatty acids or triglycerides having an increased content of fatty acids containing at least three double bonds, wherein the substrate used for the reaction of the $\Delta$-8-desaturase, $\Delta$-9-elongase and/or $\Delta$-5-desaturase is preferably—linoleic acid ($C_{20:2}^{\Delta 9,12}$) acid and/or $\alpha$-linolenic acid ($C_{18:2}^{\Delta 9,12,15}$). In this way the method identified above advantageously allows in particular the synthesis of fatty acids derived from linoleic acid ($C_{20:2}^{\Delta 9,12}$), $\alpha$-linolenic acid ($C_{18:2}^{\Delta 9,12,15}$) $\gamma$-linoleic acid ($C_{18:3}^{\Delta 6,9,12}$), stearidonic acid ($C_{18:4}^{\Delta 6,9,12,15}$), dihomo-$\gamma$-linoleic acid ($C_{20:3}^{\Delta 8,11,14}$) or such as by way of example eicosapentaenoic acid and arachidonic acid.

Examples of organisms for the said methods as described above are plants such as *Arabidopsis, Primulaceae*, borage, barley, wheat, rye, oats, corn, soybean, rise, cotton, sugar beet, oilseed rape and canola, sunflower, flax, hemp, potatoes, tobacco, tomatoes, rape, tapioca, cassava, arrowroot, alfalfa, peanut, castor oil plant, coconut, oil palm, safflower (*Carthamus tinctorius*) or cocoa bean, microorganisms such as the fungi *Mortierella, Saprolegnia* or *Pythium*, bacteria such as the genus *Escherichia*, cyanobacteria, yeasts such as the genus *Saccharomyces*, algae or protozoa such as dinoflagellates like *Crypthecodinium*. Preference is given to organisms which can naturally synthesize oils in relatively large quantities such as fungi like *Mortierella alpina, Pythium insidiosum* or plants such as soybean, oilseed rape, coconut, oil palm, safflower, castor oil plant, *Calendula*, peanut, cocoa bean or sunflower, or yeasts such as Saccharomyces cerevisiae and particular preference is given to soybean, oilseed rape, sunflower, flax, *Primulaceae*, borage, *Carthamus* or *Saccharomyces cerevisiae*.

Depending on the host organism, the organisms used in the methods are grown or cultured in the manner known to those skilled in the art. Microorganisms such as fungi or algae are usually grown in a liquid medium containing a carbon source, usually in the form of sugars, a nitrogen source, usually in the form of organic nitrogen sources such as yeast extract or salts such as ammonium sulfate, trace elements such as iron, manganese or magnesium salts and optionally vitamins at temperatures of between 10° C. and 60° C., preferably between 15° C. and 40° C. with exposure to gaseous oxygen. In doing so the pH of the nutrient liquid may be kept at a fixed value, that is during growth it is or is not regulated. Growth can ensue in batch mode, semibatch mode or continuously. Nutrients can be provided at the start of fermentation or be fed in semicontinuously or continuously.

After transformation plants are first of all regenerated as described above and then cultured or cultivated as normal.

After growth the lipids are isolated from the organisms in the usual way. For this purpose, after harvesting the organisms may first of all be digested or used directly. The lipids are advantageously extracted using suitable solvents such as a polar solvents like hexane or ethanol, isopropanol or mixtures such as hexane/isopropanol, phenol/chloroform/isoamyl alcohol at temperatures of between 0° C. and 80° C., preferably between 20° C. and 50° C. The biomass is usually extracted with an excess of solvent, for example an excess of solvent to biomass of 1:4. The solvent is then removed, for example by distillation. Extraction can also be done using supercritical $CO_2$. After extraction the remaining biomass may be removed, for example by filtration.

The crude oil isolated in this way can then be further purified, for example by removing cloudiness by treatment with polar solvents such as acetone or chloroform and then filtration or centrifugation. Further purification through columns is also possible.

In order to obtain the free acids from the triglycerides the latter are saponified in the usual way.

A further object of the invention comprises unsaturated fatty acids and triglycerides having an increased content of unsaturated fatty acids produced by the methods identified above and use thereof for producing foods, animal feeds, cosmetics or pharmaceuticals. For this purpose the latter are added in customary quantities to the foods, the animal feed, the cosmetics or pharmaceuticals.

Said unsaturated fatty acids according to the invention as well as triglycerides having an increased content of unsaturated fatty acids produced by the methods identified above are the result of the expression of the nucleic acids according to the invention in the various host organisms. This results overall in a modification of the composition of the compounds in the host cell containing unsaturated fatty acids by comparison with the original starting host cells which do not contain the nucleic acids. These modifications are more marked in host organisms, for example plant cells, which naturally do not contain the proteins or enzymes encoded by the nucleic acids than in host organisms which naturally do contain the proteins or enzymes encoded by the nucleic acids. This gives rise to host organisms containing oils, lipids, phospholipids, sphingofipids, glycoipids, triacylglycerols and/or free fatty acids having a higher content of PUFAs with at least three double bonds. For the purposes of the invention, by an increased content is meant that the host organisms contain at least 5%, advantageously at least 10%, preferably at least 20%, particularly preferably at least 30%, most particularly preferably at least 40% more polyunsaturated fatty acids by comparison with the initial organism which does not contain the nucleic acids according to the invention. This is particularly the case for plants which do not naturally contain longer-chain polyunsaturated $C_{20}$ or $C_{22}$ fatty acids such as EPA or ARA. Due to the expression of the nucleic adds novel lipid compositions are produced by said means these being a further aspect of the invention.

The invention is explained in more detail by the following examples.

EXAMPLES

Example 1

General Cloning Methods

The cloning methods, such as by way of example restriction cleavages, agarose gel electrophoresis, purification of DNA fragments, transfer of nucleic acids to nitrocellulose and nylon membranes, linkage of DNA fragments, transformation of—*Escherichia coli* cells, culture of bacteria and sequence analysis of recombinant DNA, were carried out as described in Sambrook et al. (1989) (Cold Spring Harbor Laboratory Press: ISBN 0-87969-309-6).

Example 2

Sequence Analysis of Recombinant DNA

Sequencing of recombinant DNA molecules was done using a laser fluorescence DNA sequencer from the ABI company by the method of Sanger (Sanger et al. (1977) Proc. Natl. Acad. Sci. USA74, 54635467). Fragments resulting from a polymerase chain reaction were sequenced and checked to prevent polymerase errors in the constructs to be expressed.

Example 3

Cloning of the Δ-8-Desaturase from *Euglena gracilis*
(=SEQ ID NO: 1)

As a template for PCR amplification, cDNA from *Euglena gracilis* Strain Z was used. The cDNA was synthesised from total RNA extracted from cultures of *E. gracilis* strain Z. Unique primers to the initiating methionine and the stop codon of the *Euglena* Δ-8-desaturase were synthesized as shown, including restriction sites as detailed

```
Primer 1:
EDELTA8BamF    ATGGATCCACCATGAAGTCAAAGCGCCAA
               (SEQ ID NO: 11)

Primer 2:
EDELTA8XhoR    ATCTCGAGTTATAGAGCCTTCCCCGC
               (SEQ ID NO: 12)

PCR protocol
```

Addition temperature: 1 min at 45° C.

Denaturing temperature: 1 min at 94° C.

Elongation temperature: 2 min at 72° C.

Number of cycles: 30

The PCR products were separated on an agarose gel and a 1270 bp fragment was isolated. The PCR fragment was cloned in the pGEM-T easy vector (Promega) and the insert was then sequenced. This revealed the presence of an open reading frame of 1266 base pairs, encoding a protein of 421 amino acid residues and a stop codon. The C-terminals of the cloned Δ-8-desaturase has high homologies to the Δ-8-desaturase published by Wallis and Browse (Archives of Biochem. and Biophysics, Vol. 365, No. 2, 1999) which is reported to be an enzyme of 422 residues; see also related sequence by these authors [GenBank AF139720/AAD45877] which purports to relate to the same Δ-8-desaturase but describes an open reading frame of 419 residues]. The deduced amino acid sequence the *Euglena* Δ-8-desaturase described in this present invention differs from that previously described by heterogeneity at the N-terminus. In particular, the first 25 amino acid residues of LARS Δ-8-desaturase is:

```
MKSKRQALP LTIDGTTDVS AWVNF
(SEQ ID NO: 13)
```

Whereas the sequence described by Wallis & Browse is:

```
MKSKRQALS PLQLMEQTYDV SAWVN
(SEQ ID NO: 14)
```

Or, alternatively

```
MKSKRQALSPLQLMEQTYDVVNFH
(SEQ ID NO: 15)
```

(as given in GenBank AAD45877)

Said heterogeneity present at the N-terminus of the desaturase sequence is not resultant of the PCR amplification or primers. The distinctions are true differences between the proteins.

Example 4

Construction of Transgenic Plants Expressing the
*Isochrysis galbana* Elongase Component IgASE1

The cloning of IgASE1 cDNA is described in: Qi, B., Beaudoin, F., Fraser, T., Stobart, A. K., Napier, J. A. and Lazarus, C. M. Identification of a cDNA encoding a novel C18-Δ-9-polyunsaturated fatty acid-specific elongating activity from the docosahexaenoic acid (DHA)-producing microalga, *Isochrysis galbana*. FEBS Letters 510, 159-165 (2002). The cDNA was released from plasmid vector pCR2.1-TOPO by digestion with KpnI, and ligated into the KpnI site of the intermediate vector pBlueBac 4.5 (Invitrogen). Recombinant plasmids were screened for insert orientation with EcoRI. The insert was released from a selected plasmid with PstI plus EcoRI and ligated into binary vector plasmid pCB302-1 (Xiang et al, 1999) that had been cut with the same enzymes. This placed the IgASE1 coding region under the control of the CaMV 35S promoter as a translational fusion with the transit peptide of the small subunit of Rubisco (Xiang at al., 1999), with the intention of targeting the elongase component to chloroplasts when expressed in transgenic plants. This recombinant binary vector was designated pCB302-1ASE. To construct a similar vector with expression of the elongase component targeted to the microsomal membrane, the IgASE1 coding region was removed from the intermediate vector by digestion with BamHI plus SpeI, and ligated into the corresponding sites of pCB302-3 (Xiang et al., 1999, in which the map of pCB302-3 is incorrect the CaMV 35S promoter (plus omega sequence)

and nos terminator regions are reversed with respect to MCS2). This recombinant binary vector was designated pCB302-3ASE.

Example 5

Plant Expression of the Elongase

Binary vectors were transferred to *Agrobacterium tumefaciens* strain GV3101 by electroporation; transformed colonies were selected on medium containing 50 µg ml$^{-1}$, kanamycin. Selected colonies were gown to stationary phase at 28° C., then the cells were concentrated by centrifugation and resuspended in a dipping solution containing 5% sucrose, 0.03% Silwet-177 and 10 mM MgCl$_2$.

Seeds of *Arabidopsis thaliana* ecotype Columbia 4 were germinated on one-half-strength Murashige and Skoog medium, and seedlings were transferred to compost in 15 cm flower pots. Plants were grown to flowering stage in a growth cabinet at 21° C., with a 23 light and 1 hour dark cycle. Plant transformation was carried out by the floral dipping method of Clough and Bent (1998, Floral dip: a simplified method for *Agrobacterium*-mediated transformation of *Arabidopsis thaliana*. Plant Journal 16, 735-743 (1998), essentially as follows:

For each construct two pots containing 16 plants were inverted in the dipping solutions containing transformed *A. tumefaciens* (described above). The plants were then covered with a plastic bag and left at room temperature in the dark overnight. The bag was then removed and the plants transferred to the growth cabinet. Dipping (with fresh *A. tumefaciens* solutions) was repeated after 5 days and the plants were allowed to set seed. Bulked seed from dipped plants (=T1 seed) was collected, and approximately 10000 seed sprinkled onto compost in a seed tray, and, after stratification at 4° C. for 2 days, cultivated in the growth cabinet. When seedlings had reached the 2 to 4 trueleaf stage they were sprayed with Liberty herbicide (Aventis, 0.5 g glufosinate-ammonium ml$^{-1}$), and spraying was repeated one week later. Twelve herbicide-resistant plants were selected and potted on for each line (chloroplast or cytoplasm targeted elongase component), and allowed to self fertilize. Samples of T2 seed collected from these plants were germinated on one-half-strength Murashige and Skoog medium containing Liberty (5 mg glufosinate-ammonium ml$^{-1}$). T3 seed collected from individual surviving plants was then again germinated on Liberty plates to screen for lines that had ceased segregating for herbicide resistance. Total fatty acids extracted from leaves of such lines were analysed and those with the greatest C20 content (CB12-4 with the chloroplast-targeted elongase component and CA1-9 with the cytoplasm-targeted elongase component) selected.

Example 6

Production of Transgenic Plants Expressing the *Isochrysis galbana* Elongase Component IgASE1 and the *Euglena gracilis* Δ8 Desaturase EUGD8

The Δ-8-desaturase coding region was removed from the yeast expression vector pESC-Trp with BamHI plus XhoI, ligated into the BamHI and XhoI sites of pBlueBac 4.5 (Invitrogen) and transformed into *E. coli* strain Tam 1. The insert was removed from a recombinant plasmid with BgI and BamHI, ligated into the BamHI site of pBECKS$_{19}$.6 and transformed into *E. coli* strain Tam1. DNA minipreparations were made of the recombinant plasmids of 6 transformant colonies; these were digested with XhoI to determine the orientation of insertion of the desaturase coding region in the binary vector. One recombinant plasmid with the insert in the correct orientation for expression from the CaMV 35S promoter was transferred to *Agrobacterium tumefaciens* strain GV3101 by electroporation and a dipping solution prepared from a transformed colony as described above.

*Arabidopsis thaliana* lines CB12-4 and CA1-9 (see above) were subjected to floral dipping as described above. Approximately 2000 T1-seed from each line were spread on 15 cm petri dishes containing one-half-strength Murashige and Skoog (solid) medium supplemented with 50 µg ml$^{-1}$ kanamycin and germinated in the growth cabinet. 12 kanamycin-resistant plants of the CA1-9 parental line and 3 plants of the CB12-4 parental line were transferred to potting compost and further cultivated in the growth room. Fatty acid analysis was conducted on a lea taken from each of the T2 plants, which were allowed to mature and set seed.

REFERENCES

McCormac, A. C., Eliott, M. C. and Chen, D-F.; pBECKS. A flexible series of binary vectors for *Agrobacterium*-mediated plant transformation. *Molecular Biotechnology* 8, 199-213 (1997).
Xiang, C., Han, P., Lutziger, I., Wang, K. and Oliver, D. J.; A mini binary vector series for plant transformation. *Plant Molecular Biology* 40, 711-717 (1999).

Example 7

Production of Transgenic Plants Expressing the *Isochrysis galbana* Elongase Component IgASE1 and the *Euglena gracilis* Δ8 Desaturase EUGD8 and a Δ5 Desaturase The Δ5 desaturase from *Phaeodactylum tricornutum* was cloned into the pGPTV plasmid (Becker, D. et al.; Plant Mol. Biol. 20 (1992), 1195-1197) harboring a hygromycin resistence selectable marker gene. For seed-specific expression the USP promoter from Vicia faber was cloned 5'-prime to the ATG of the Δ5 desaturase.

The binary vector was transferred to *Agrobacterium tumefaciens* strain GV 3101 and transformed colonies were selected on medium containing 30 µg ml$^{-1}$ hygromycin. Selected *Agrobacteria* were used for the transformation (flower transformation) of *Arabidopsis* plants carrying the T-DNA insertions with the Δ9 elongase and the Δ5 desaturase.

*Arabidopsis thaliana* seedlings were germinated on Murashige and Skoog medium containing hygromycin and resistent plants were transferred to the greenhouse.

Seeds collected from individual plants were harvested and the total fatty acid profile was analyzed using GC methods.

Example 8

Cloning of Expression Plasmids for Seed-Specific Expression in Plants pBin-USP is a derivative of the plasmid pBin19. pBin-USP was produced from pBin19 by inserting a USP promoter as an EcoRI-BaMHI fragment into pBin19 (Bevan et al. (1980) Nucl. Acids Res. 12, 8711). The polyadenylation signal is that of gene 3 of the T-DNA of the Ti plasmid pTiACH5 (Gielen et al., (1984) EMBO J. 3, 835), whereby nucleotides 11749-11939 were isolated as a PvuII-HindIII fragment and after addition of SphI linkers to the PvuII interface between the SpHI-HindIII interface of the vector were cloned. The USP promoter corresponds to nucleotides 1-684 (gene bank accession number X56240), wherein a part of the nonencoding region of the USP gene is contained in the promoter. The promoter fragment running to 684 base pairs was amplified by standard methods by means of commercial T7 standard primer (Stratagene) and using a synthesized primer through a PCR reaction.

Primer sequence:

```
5'-GTCGACCCGCGGACTAGTGGGCCCTCTAGACCCGGGGATCC
GGATCTGCTGGCTATGAA-3'
(SEQ ID NO: 16)
```

The PCR fragment was cut again using EcoRI/SalI and inserted into the vector pBin19 with OCS terminator. The plasmid having the designation pBinUSP was obtained. The constructs were used for transforming Arabidopsis thaliana, oilseed rape, tobacco and linseed.

Example 9

Production of Transgenic Oil Crops

Production of transgenic plants (modified in accordance with Moloney et al., 1992, Plant Cell Reports, 8:238-242)

To produce transgenic oilseed rape plants binary vectors in Agrobacterium tumefaciens C58C1:pGV2260 or Escherichia coli were used (Deblaere et al, 1984, Nucl. Acids. Res. 13, 4777-4788). For transforming oilseed rape plants (var. Drakkar, NPZ Nordeutsche Pflanzenzucht, Hohenlieth, Germany) a 1:50 dilution of an overnight culture of a positively transformed agrobacteria colony in Murashige-Skoog medium (Murashige and Skoog 19862 Physiol. Plant. 15, 473) containing 3% of saccharose (3MS medium) was used. Petioles or hypocotyledons of freshly germinated sterile rape plants (approx 1 cm² each) were incubated in a Petri dish with a 1:50 agrobacteria dilution for 5-10 minutes. This was followed by 3-day concubation in darkness at 25° C. on 3MS medium containing 0.8% of Bacto-Agar. After three days, culturing was continued with 16 hours of light/8 hours of darkness and in a weekly cycle on MS medium containing 500 mg/l of Claforan (sodium cefotaxime), 50 mg/l of kanamycin, 20 microM of benzylaminopurine (BAP) and 1.6 g/l of glucose. Growing shoots were transferred onto MS medium containing 2% of saccharose, 250 mg/l of Claforan and 0.8% of Bacto-Agar. If after three weeks no roots had formed 2-indolylbutyric acid was added to the medium as a growth hormone for rooting purposes.

Regenerated shoots were obtained on 2MS medium using kanamycin and Claforan, transferred into soil after rooting and after culturing grown for two weeks in a climate-controlled chamber, brought to blossom and after harvesting of ripe seed investigated for Δ-8-desaturase expression by means of lipid analyses. Ones having increased contents of double bonds at the Δ-8-position were identified. In the stably transformed transgenic lines functionally expressing the transgene it was found that there is an increased content of double bonds at the Δ-8-position by comparison with untransformed control plants.

The same procedure was done to create plants with Δ-9-elongase and/or Δ-5-desaturase activity.

a) Transgenic Flax Plants

Transgenic flax plants may be produced, for example by the by the method Bell et al., 1999, In Vitro Cell. Dev. Biol.-Plant. 35(6):456-465, by means of partide bombardment. Agrobacteria-mediated transformations can be produced, for example, as described by Mlynarova et al. (1994), Plant Cell Report 13: 282-285.

Example 10

Lipid Extraction from Seed and Leave Material

Plant material (approx 200 mg) was first of all mechanically homogenized by means of triturators in order to render it more amenable to extraction.

The disrupted cell sediment was hydrolyzed with 1 M methanoric hydrochloric add and 5% dimethoxypropane for 1 h at 85° C. and the lipids were transmethylated. The resultant fatty acid methyl esters (FAMES) were extracted in hexane. The extracted FAMEs were analyzed by gas-liquid chromatograph using a capillary column (Chrompack, WCOT fused silica, CP wax 52 CB, 25 m, 0.32 mm) and a temperature gradient of from 170° C. to 240° C. in 20 min and 5 min at 240° C. The identity of the fatty add methyl esters was confirmed by comparison with corresponding FAME standards (Sigma). The identity and the position of the double bond was further analyzed by means of GC-MS by suitable chemical derivatization of the FAME mixtures, e.g. to form 4,4-dimethoxyoxazoline derivatives (Christie, 1998).

Figure 2:
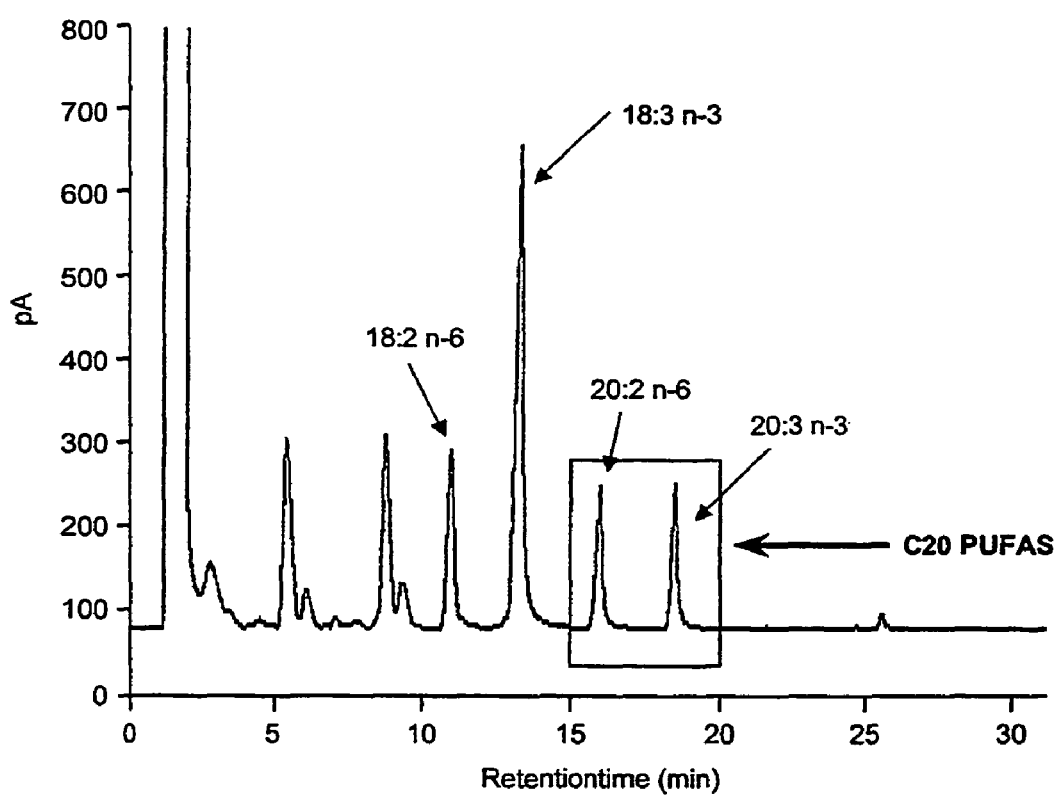
FIG. 2 shows the fatty acid profile (FAMes) of leaf tissue from trausgenic *Arabidopsis* expressing the *Isochrysis* Δ-9-elongase (see example 4).
Figure 3:
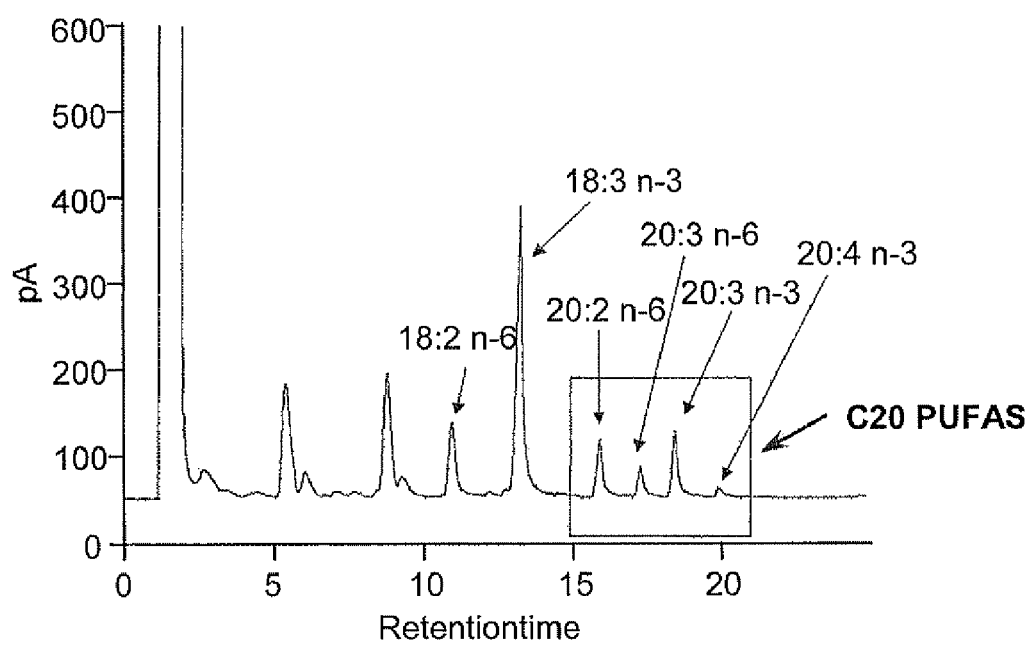
FIG. 3 shows the fatty acid profile (FAMes) of the double transformed *Arabidopsis* line expressing the *Isochrysis* Δ-9-elongase and the *Euglena* Δ-8-desaturase (Line IsoElo X Eu D8 des).

FIG. 1 shows the fatty acid profile (FAMes) of leaf tissue from wildtype Arabidopsis thaliana as a control. FIG. 2 shows the fatty acid profile (FAMes) of leaf tissue from transgenic Arabidopsis expressing the Isochrysis Δ-9-elongase (see example 4). This Arabidopsis line was subsequently retransformed with the Euglena Δ-8-desaturase. The fatty acid profile (FAMes) of said double transformed Arabidopsis line (Line IsoEIo X Eu D8 des) is given in FIG. 3.

Figure 4:
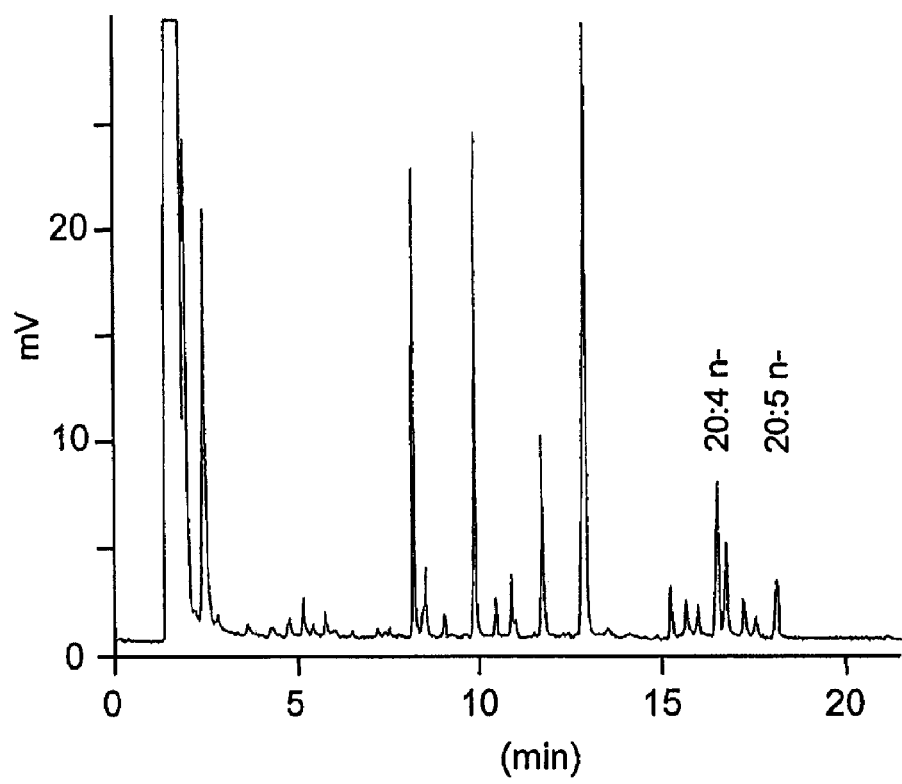
FIG. 4 shows the fatty acid profile (FAMes) of the triple transformed *Arabidopsis* line expressing the *Isocbrysis* Δ-9-elongase, the *Euglena* Δ-8-desaturase, and the *Mortierella* Δ5 desaturase (Mort Δ5) gene (Line IsoElo X EU D8 des x Mort Δ5).
Figure 5A:
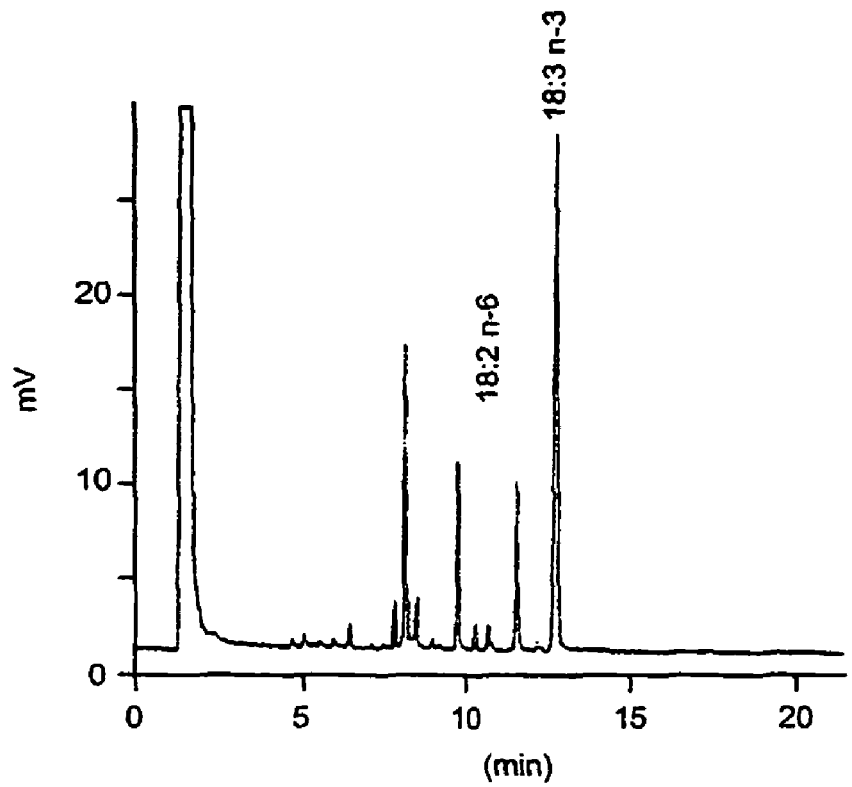
FIG. 5 shows GC profiles of *Arabidopsis* leaf fatty acid methyl esters extracted from wild type (FIG. 5A), single transgenic plants expressing *Isochrysis galbana* Δ9 elongase gene Ig ASE1 (FIG. 5B), double transgenic plant expressing the Ig ASE1 and *Euglena* Δ8 desaturase (EU Δ8) genes (FIG. 5C), and the triple transfenic plant expressing the Ig ASE1, Eu Δ8 and the *Mortierella* Δ5 desaturase (Mort Δ5) genes (FIG. 5D).
Figure 5B:
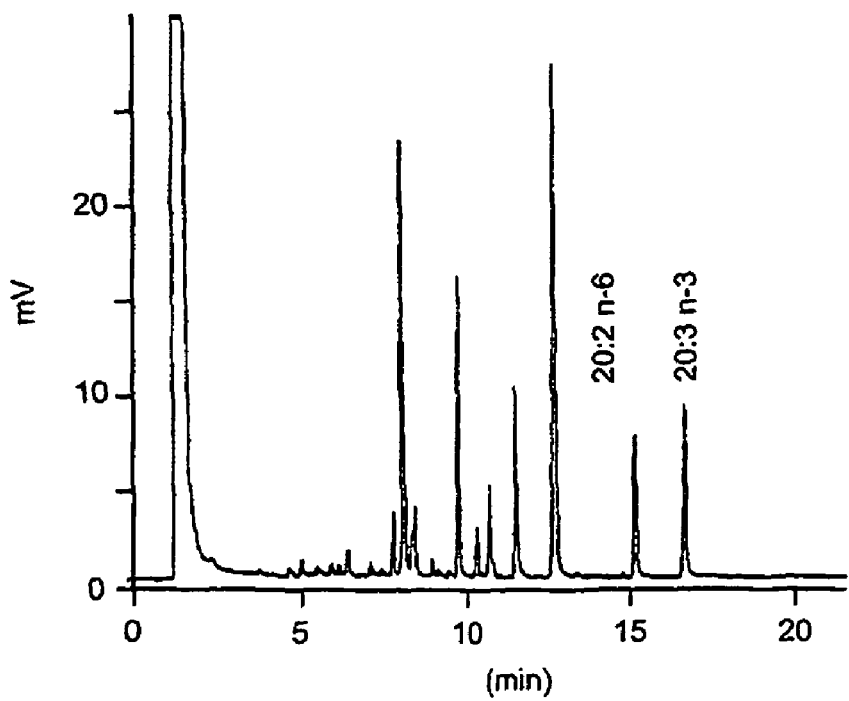
Figure 5C:
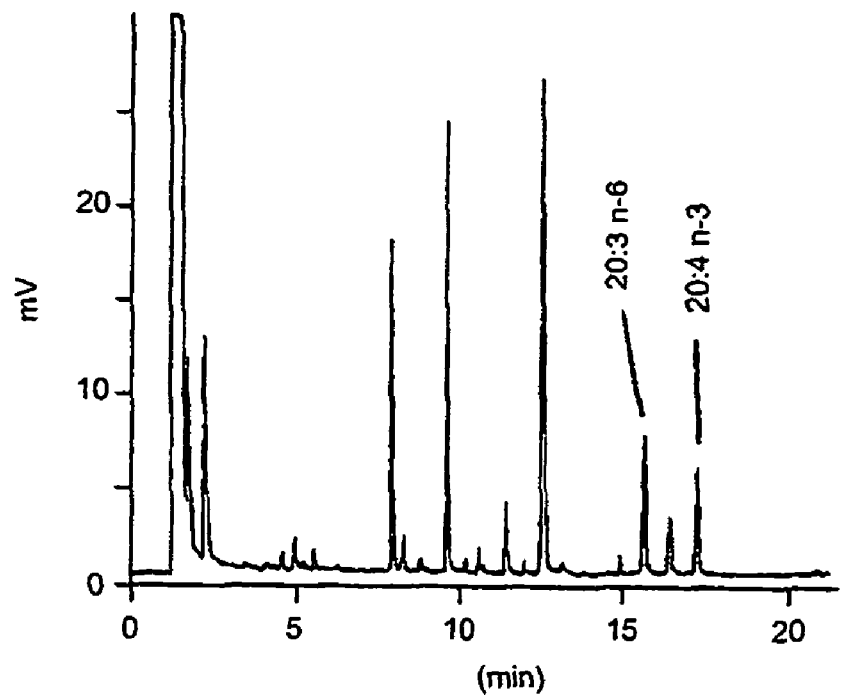
Figure 5D:
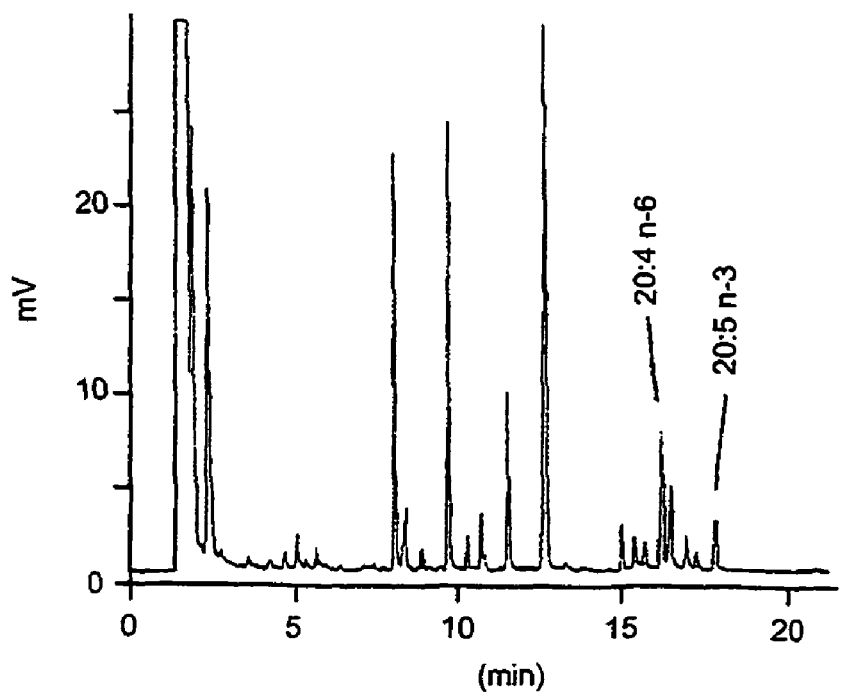

Furthermore this double transformed Arabidopsis line (Line IsoEIo×Eu D8 des) was subsequently re-transformed with the Mortierella Δ5 desaturase (Mort Δ5) gene. The fatty acid profile (FAMes) of said triple transformed Arabidopsis line (Line IsoEIo×EU D8 des×Mort Δ5) is given in FIG. 4.

Example 11

GC Profiles of Arabidopsis Leaf Fatty Acid Methyl Esters from Different Transgenics FIG. 5 shows GC profiles of Arabidopsis leaf fatty acid methyl esters extracted from wild type (WT 5a), single transgenic plants expressing Isochrysis galbana Δ9 elongase gene Ig ASE1 (5b), double transgenic plant expressing the Ig ASE1 and Euglena Δ8 desaturase (EU Δ8) genes (5c) and the triple transfehic plant expressing the Ig ASE1, Eu Δ8 and the Mortierella Δ5 desaturase (Mort Δ5) genes (5d).

Table 1 shows the fatty acid composition of Arabidopsis plants prepared from wild type (Wt), single transgenic plant expressing the Isochrysis galbana IgASE1 elongase gene, double transgenic plants expressing the IgASE1 elongase gene and the Euglena Δ8 desaturase gene and triple transgenic plants expressing the IgASE1, the Euglena Δ8 and the Mortierella Δ5 desaturase gene. Analysis is of leaf tissue from rosette stage Arabidopsis plants. Each value represents the average of 2 measurements.

| Fatty acid (mol % of total) | Plant source | | | |
|---|---|---|---|---|
| | Wt | IgASE1 transgenic | IgASE1 + EuΔ8 transgenic | IgASE1 + EuΔ8 + MortΔ5 transgenic |
| 16:0 | 19.9 | 19.2 | 14.7 | 14.2 |
| 16:1 | 2.8 | 3.3 | 1.8 | 2.3 |
| 16:3 | 13.1 | 12.2 | 19.9 | 15.4 |
| 18:0 | 1.7 | 2.4 | 0.8 | 1.5 |
| 18:1n-9 | 1.7 | 5.1 | 1.6 | 3.4 |
| 18:2n-6 | 11.2 | 9.0 | 4.2 | 6.6 |
| 18:3n-3 | 50.1 | 31.0 | 36.0 | 31.2 |
| 20:2n-6 | — | 7.9 | 0.9 | 3.2 |
| 20:3, Δ5, 11, 14 | — | | | 1.5 |
| 20:3n-6 | — | — | 9.1 | 1.5 |
| 20:4n-6 (ARA) | — | — | — | 6.6 |
| 20:3n-3 | — | 9.9 | 4.0 | 4.8 |
| 20:4Δ5, 11, 14, 17 | — | — | — | 1.6 |
| 20:4n-3 | — | — | 7.2 | 2.9 |
| 20:5n-3 (EPA) | — | — | — | 3.3 |
| Total C20 PUFAs | — | 17.8 | 21.2 | 22.2 |

All transgenes are under the control of the 35S-CaMV viral promoter. *Isochrysis* Δ9 elongase (IgASE1) with SSU Rubisco transit sequence [T-DNA Basta-r] were retransformed with *Euglena* Δ8-desaturase$^{mut175+313}$ [T-DNA Kanamycin-r]. The double transformed line, which is homozygous for both Basta-r and Kanamycin-r, were transformed again with *Mortierella* Δ5 desaturase (T-DNA Hygromycin-r). The resulting triple transformed line is homozygous for both Basta-r and Kanamycin-r, but heterozygous for Hygromycin-r.

What is claimed is:

1. A process for the production of one or more $C_{16}$-, $C_{18}$-, and/or $C_{20}$-polyunsaturated fatty acids in a transgenic organism comprising:
   a) introducing at least one nucleic acid sequence encoding a Δ-9-elongase into an organism, wherein said Δ-9-elongase comprises the amino acid sequence of SEQ ID NO: 4,
   b) introducing at least one second nucleic acid sequence encoding a Δ-8-desaturase, wherein the Δ-8-desaturase comprises the amino acid sequence of SEQ ID NO: 2,
   c) introducing at least one third nucleic acid sequence encoding a Δ-5-desaturase, wherein the Δ-5-desaturase comprises the amino acid sequence of SEQ ID NO: 6, and
   d) cultivating and harvesting said organism, wherein said organism is a plant or a microorganism.

2. The process of claim 1, wherein the nucleic acid sequence encoding a Δ-9-elongase comprises the nucleic acid sequence of SEQ ID NO: 3.

3. The process of claim 1, wherein the nucleic acid sequence encoding a Δ-8-desaturase comprising the nucleic acid sequence of SEQ ID NO: 1.

4. The process of claim 1, wherein the nucleic acid sequence encoding a Δ-5-desaturase comprises the nucleic acid sequence of SEQ ID NO: 5.

5. The process of claim 1, wherein the nucleic acid sequence encoding a Δ-9-elongase comprises the nucleic acid sequence of SEQ ID NO: 3, the nucleic acid sequence encoding a Δ-8-desaturase comprising the nucleic acid sequence of SEQ ID NO: 1, and the nucleic acid sequence encoding a Δ-5-desaturase comprises the nucleic acid sequence of SEQ ID NO: 5.

6. The process of claim 1, wherein the plant is an oil producing plant.

7. The process of claim 6, wherein the oil producing plant is selected from the group consisting of rapeseed, poppy, mustard, hemp, castor bean, sesame, olive, calendula, punica, hazel nut, almond, macadamia, avocado, pumpkin, walnut, laurel, pistachio, primrose, canola, peanut, linseed, soybean, safflower, sunflower and borage.

8. The process of claim 1, wherein the polyunsaturated fatty acids are isolated in the form of oils, lipids of free fatty acids.

9. The process of claim 1, wherein the polyunsaturated fatty acids have at least two double bonds.

10. A process for the production of compounds comprising one or more $C_{16}$-, $C_{18}$-, and/or $C_{20}$-polyunsaturated fatty acids in a transgenic organism comprising:
   a) introducing at least one nucleic acid sequence encoding a Δ-9-elongase into an organism, wherein said Δ-9-elongase comprises the amino acid sequence of SEQ ID NO: 4,
   b) introducing at least one second nucleic acid sequence encoding a Δ-8-desaturase, wherein the Δ-8-desaturase comprises the amino acid sequence of SEQ ID NO: 2,
   c) introducing at least one third nucleic acid sequence encoding a Δ-5-desaturase, wherein the Δ-5-desaturase comprises the amino acid sequence of SEQ ID NO: 6, and
   d) cultivating and harvesting said organism, wherein said organism is a plant or a microorganism.

11. The process of claim 10, wherein the nucleic acid sequence encoding a Δ-9-elongase comprises the nucleic acid sequence of SEQ ID NO: 3.

12. The process of claim 10, wherein the nucleic acid sequence encoding a Δ8-desaturase comprising the nucleic acid sequence of SEQ ID NO: 1.

13. The process of claim 10, wherein the nucleic acid sequence encoding a Δ-5-desaturase comprises the nucleic acid sequence of SEQ ID NO: 5.

14. The process of claim 10, wherein the nucleic acid sequence encoding a Δ-9-elongase comprises the nucleic acid sequence of SEQ ID NO: 3, the nucleic acid sequence encoding a Δ-8-desaturase comprising the nucleic acid sequence of SEQ ID NO: 1, and the nucleic acid sequence encoding a Δ-5-desaturase comprises the nucleic acid sequence of SEQ ID NO: 5.

15. The process of claim 10, wherein the plant is an oil producing plant.

16. The process of claim 15, wherein the oil producing plant is selected from the group consisting of rapeseed, poppy, mustard, hemp, castor bean, sesame, olive, calendula, punica, hazel nut almond, macadamia, avocado, pumpkin, walnut, laurel, pistachio, primrose, canola, peanut, linseed, soybean, safflower, sunflower and borage.

17. The process of claim 10, wherein the compounds are isolated in the form of oils, lipids of free fatty acids.

18. The process of claim 10, wherein the polyunsaturated fatty acids have at least two double bonds.

19. A process for increasing the content of fatty acids, oils or lipids containing $C_{16}$-, $C_{15}$-, and/or $C_{20}$-polyunsaturated fatty acids in an organism comprising:
   a) introducing at least one nucleic acid sequence encoding a Δ-9-elongase into an organism, wherein said Δ-9-elongase comprises the amino acid sequence of SEQ ID NO: 4,
   b) introducing at least one second nucleic acid sequence encoding a Δ-8-desaturase, wherein the Δ-8-desaturase comprises the amino acid sequence of SEQ ID NO: 2,
   c) introducing at least one third nucleic acid sequence encoding a Δ-5-desaturase, wherein the Δ-5-desaturase comprises the amino acid sequence of SEQ ID NO: 6, and
   d) cultivating and harvesting said organism, wherein said organism is a plant or a microorganism.

20. The process of claim 19, wherein the nucleic acid sequence encoding a Δ-9-elongase comprises the nucleic acid sequence of SEQ ID NO: 3.

21. The process of claim 19, wherein the nucleic acid sequence encoding a Δ-8-desaturase comprising the nucleic acid sequence of SEQ ID NO: 1.

22. The process of claim 19, wherein the nucleic acid sequence encoding a Δ-5-desaturase comprises the nucleic acid sequence of SEQ ID NO: 5.

23. The process of claim 19, wherein the nucleic acid sequence encoding a Δ-9-elongase comprises the nucleic acid sequence of SEQ ID NO: 3, the nucleic acid sequence encoding a Δ-5-desaturase comprising the nucleic acid sequence of SEQ ID NO: 1, and the nucleic acid sequence encoding a Δ-5-desaturase comprises the nucleic acid sequence of SEQ ID NO: 5.

24. The process of claim 19, wherein the plant is an oil producing plant.

25. The process of claim 24, wherein the oil producing plant is selected from the group consisting of rapeseed, poppy, mustard, hemp, castor bean, sesame, olive, calendula, punica, hazel nut, almond, macadamia, avocado, pumpkin, walnut, laurel, pistachio, primrose, canola, peanut, linseed, soybean, safflower, sunflower and borage.

26. The process of claim 19, wherein the polyunsaturated fatty acids have at least two double bonds.

* * * * *

SEQUENCE LISTING

<160> NUMBER OF SEQ ID NOS: 16

<210> SEQ ID NO 1
<211> LENGTH: 1266
<212> TYPE: DNA
<213> ORGANISM: Euglena gracilis
<220> FEATURE:
<221> NAME/KEY: CDS
<222> LOCATION: (1)..(1266)
<223> OTHER INFORMATION: delta-8-desaturase

<400> SEQUENCE: 1

```
atg aag tca aag cgc caa gcg ctt ccc ctt aca att gat gga aca aca        48
Met Lys Ser Lys Arg Gln Ala Leu Pro Leu Thr Ile Asp Gly Thr Thr
 1               5                  10                  15 tat gat gtg tct gcc tgg gtc aat ttc cac cct ggt ggt gcg gaa att        96
Tyr Asp Val Ser Ala Trp Val Asn Phe His Pro Gly Gly Ala Glu Ile
             20                  25                  30 ata gag aat tac caa gga agg gat gcc act gat gcc ttc atg gtt atg       144
Ile Glu Asn Tyr Gln Gly Arg Asp Ala Thr Asp Ala Phe Met Val Met
         35                  40                  45 cac tct caa gaa gcc ttc gac aag ctc aag cgc atg ccc aaa atc aat       192
His Ser Gln Glu Ala Phe Asp Lys Leu Lys Arg Met Pro Lys Ile Asn
     50                  55                  60 ccc agt tct gag ttg cca ccc cag gct gca gtg aat gaa gct caa gag       240
Pro Ser Ser Glu Leu Pro Pro Gln Ala Ala Val Asn Glu Ala Gln Glu
 65                  70                  75                  80 gat ttc cgg aag ctc cga gaa gag ttg atc gca act ggc atg ttt gat       288
Asp Phe Arg Lys Leu Arg Glu Glu Leu Ile Ala Thr Gly Met Phe Asp
                 85                  90                  95 gcc tcc ccc ctc tgg tac tca tac aaa atc agc acc aca ctg ggc ctt       336
Ala Ser Pro Leu Trp Tyr Ser Tyr Lys Ile Ser Thr Thr Leu Gly Leu
            100                 105                 110 gga gtg ctg ggt tat ttc ctg atg gtt cag tat cag atg tat ttc att       384
Gly Val Leu Gly Tyr Phe Leu Met Val Gln Tyr Gln Met Tyr Phe Ile
        115                 120                 125 ggg gca gtg ttg ctt ggg atg cac tat caa cag atg ggc tgg ctt tct       432
```

```
Gly Ala Val Leu Leu Gly Met His Tyr Gln Gln Met Gly Trp Leu Ser
        130                 135                 140 cat gac att tgc cac cac cag act ttc aag aac cgg aac tgg aac aac      480
His Asp Ile Cys His His Gln Thr Phe Lys Asn Arg Asn Trp Asn Asn
145                 150                 155                 160 ctc gtg gga ctg gta ttt ggc aat ggt ctg caa ggt ttt tcc gtg aca      528
Leu Val Gly Leu Val Phe Gly Asn Gly Leu Gln Gly Phe Ser Val Thr
                165                 170                 175 tgc tgg aag gac aga cac aat gca cat cat tcg gca acc aat gtt caa      576
Cys Trp Lys Asp Arg His Asn Ala His His Ser Ala Thr Asn Val Gln
            180                 185                 190 ggg cac gac cct gat att gac aac ctc ccc ctc tta gcc tgg tct gag      624
Gly His Asp Pro Asp Ile Asp Asn Leu Pro Leu Leu Ala Trp Ser Glu
        195                 200                 205 gat gac gtc aca cgg gcg tca ccg att tcc cgc aag ctc att cag ttc      672
Asp Asp Val Thr Arg Ala Ser Pro Ile Ser Arg Lys Leu Ile Gln Phe
    210                 215                 220 cag cag tat tat ttc ttg gtc atc tgt atc ttg ttg cgg ttc att tgg      720
Gln Gln Tyr Tyr Phe Leu Val Ile Cys Ile Leu Leu Arg Phe Ile Trp
225                 230                 235                 240 tgt ttc cag agc gtg ttg acc gtg cgc agt ctg aag gac aga gat aac      768
Cys Phe Gln Ser Val Leu Thr Val Arg Ser Leu Lys Asp Arg Asp Asn
                245                 250                 255 caa ttc tat cgc tct cag tat aag aag gag gcc att ggc ctc gcc ctg      816
Gln Phe Tyr Arg Ser Gln Tyr Lys Lys Glu Ala Ile Gly Leu Ala Leu
            260                 265                 270 cat tgg aca ttg aag gcc ctg ttc cac tta ttc ttt atg ccc agc atc      864
His Trp Thr Leu Lys Ala Leu Phe His Leu Phe Phe Met Pro Ser Ile
        275                 280                 285 ctc aca tcg ctg ttg gta ttt ttc gtt tcg gag ctg gtt ggc ggc ttc      912
Leu Thr Ser Leu Leu Val Phe Phe Val Ser Glu Leu Val Gly Gly Phe
    290                 295                 300 ggc att gcg atc gtg gtg ttc atg aac cac tac cca ctg gag aag atc      960
Gly Ile Ala Ile Val Val Phe Met Asn His Tyr Pro Leu Glu Lys Ile
305                 310                 315                 320 ggg gac tcg gtc tgg gat ggc cat gga ttc tcg gtt ggc cag atc cat     1008
Gly Asp Ser Val Trp Asp Gly His Gly Phe Ser Val Gly Gln Ile His
                325                 330                 335 gag acc atg aac att cgg cga ggg att atc aca gat tgg ttt ttc gga     1056
Glu Thr Met Asn Ile Arg Arg Gly Ile Ile Thr Asp Trp Phe Phe Gly
            340                 345                 350 ggc ttg aac tac cag atc gag cac cat ttg tgg ccg acc ctc cct cgc     1104
Gly Leu Asn Tyr Gln Ile Glu His His Leu Trp Pro Thr Leu Pro Arg
        355                 360                 365 cac aac ctg aca gcg gtt agc tac cag gtg gaa cag ctg tgc cag aag     1152
His Asn Leu Thr Ala Val Ser Tyr Gln Val Glu Gln Leu Cys Gln Lys
    370                 375                 380 cac aac ctg ccg tat cgg aac ccg ctg ccc cat gaa ggg ttg gtc atc     1200
His Asn Leu Pro Tyr Arg Asn Pro Leu Pro His Glu Gly Leu Val Ile
385                 390                 395                 400 ctg ctg cgc tat ctg gcg gtg ttc gcc cgg atg gcg gag aag caa ccc     1248
Leu Leu Arg Tyr Leu Ala Val Phe Ala Arg Met Ala Glu Lys Gln Pro
                405                 410                 415 gcg ggg aag gct cta taa                                              1266
Ala Gly Lys Ala Leu
            420

<210> SEQ ID NO 2
<211> LENGTH: 421
<212> TYPE: PRT
```

<213> ORGANISM: Euglena gracilis

<400> SEQUENCE: 2

```
Met Lys Ser Lys Arg Gln Ala Leu Pro Leu Thr Ile Asp Gly Thr Thr
 1               5                  10                  15

Tyr Asp Val Ser Ala Trp Val Asn Phe His Pro Gly Gly Ala Glu Ile
             20                  25                  30

Ile Glu Asn Tyr Gln Gly Arg Asp Ala Thr Asp Ala Phe Met Val Met
         35                  40                  45

His Ser Gln Glu Ala Phe Asp Lys Leu Lys Arg Met Pro Lys Ile Asn
     50                  55                  60

Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
             85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Cys Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Ala Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400
```

```
Leu Leu Arg Tyr Leu Ala Val Phe Ala Arg Met Ala Glu Lys Gln Pro
            405                 410                 415

Ala Gly Lys Ala Leu
            420

<210> SEQ ID NO 3
<211> LENGTH: 777
<212> TYPE: DNA
<213> ORGANISM: Isochrysis galbana
<220> FEATURE:
<221> NAME/KEY: CDS
<222> LOCATION: (1)..(777)
<223> OTHER INFORMATION: delta-9-elongase

<400> SEQUENCE: 3 atg gcc ctc gca aac gac gcg gga gag cgc atc tgg gcg gct gtg acc      48
Met Ala Leu Ala Asn Asp Ala Gly Glu Arg Ile Trp Ala Ala Val Thr
  1               5                  10                  15 gac ccg gaa atc ctc att ggc acc ttc tcg tac ttg cta ctc aaa ccg      96
Asp Pro Glu Ile Leu Ile Gly Thr Phe Ser Tyr Leu Leu Leu Lys Pro
             20                  25                  30 ctg ctc cgc aat tcc ggg ctg gtg gat gag aag aag ggc gca tac agg     144
Leu Leu Arg Asn Ser Gly Leu Val Asp Glu Lys Lys Gly Ala Tyr Arg
         35                  40                  45 acg tcc atg atc tgg tac aac gtt ctg ctg gcg ctc ttc tct gcg ctg     192
Thr Ser Met Ile Trp Tyr Asn Val Leu Leu Ala Leu Phe Ser Ala Leu
     50                  55                  60 agc ttc tac gtg acg gcg acc gcc ctc ggc tgg gac tat ggt acg ggc     240
Ser Phe Tyr Val Thr Ala Thr Ala Leu Gly Trp Asp Tyr Gly Thr Gly
 65                  70                  75                  80 gcg tgg ctg cgc agg caa acc ggc gac aca ccg cag ccg ctc ttc cag     288
Ala Trp Leu Arg Arg Gln Thr Gly Asp Thr Pro Gln Pro Leu Phe Gln
                 85                  90                  95 tgc ccg tcc ccg gtt tgg gac tcg aag ctc ttc aca tgg acc gcc aag     336
Cys Pro Ser Pro Val Trp Asp Ser Lys Leu Phe Thr Trp Thr Ala Lys
            100                 105                 110 gca ttc tat tac tcc aag tac gtg gag tac ctc gac acg gcc tgg ctg     384
Ala Phe Tyr Tyr Ser Lys Tyr Val Glu Tyr Leu Asp Thr Ala Trp Leu
        115                 120                 125 agg gtc tcc ttt ctc cag gcc ttc cac cac ttt ggc gcg ccg tgg gat     432
Arg Val Ser Phe Leu Gln Ala Phe His His Phe Gly Ala Pro Trp Asp
    130                 135                 140 gtg tac ctc ggc att cgg ctg cac aac gag ggc gta tgg atc ttc atg     480
Val Tyr Leu Gly Ile Arg Leu His Asn Glu Gly Val Trp Ile Phe Met
145                 150                 155                 160 ttt ttc aac tcg ttc att cac acc atc atg tac acc tac tac ggc ctc     528
Phe Phe Asn Ser Phe Ile His Thr Ile Met Tyr Thr Tyr Tyr Gly Leu
                165                 170                 175 acc gcc gcc ggg tat aag ttc aag gcc aag ccg ctc atc acc gcg atg     576
Thr Ala Ala Gly Tyr Lys Phe Lys Ala Lys Pro Leu Ile Thr Ala Met
            180                 185                 190 cag atc tgc cag ttc gtg ggc ggc ttc ctg ttg gtc tgg gac tac atc     624
Gln Ile Cys Gln Phe Val Gly Gly Phe Leu Leu Val Trp Asp Tyr Ile
        195                 200                 205 aac gtc ccc tgc ttc aac tcg gac aaa ggg aag ttg ttc agc tgg gct     672
Asn Val Pro Cys Phe Asn Ser Asp Lys Gly Lys Leu Phe Ser Trp Ala
    210                 215                 220 ttc aac tat gca tac gtc ggc tcg gtc ttc ttg ctc ttc tgc cac ttt     720
Phe Asn Tyr Ala Tyr Val Gly Ser Val Phe Leu Leu Phe Cys His Phe
225                 230                 235                 240 ttc tac cag gac aac ttg gca acg aag aaa tcg gcc aag gcg ggc aag     768
```

```
Phe Tyr Gln Asp Asn Leu Ala Thr Lys Lys Ser Ala Lys Ala Gly Lys
                245                 250                 255 cag ctc tag                                                                  777
Gln Leu <210> SEQ ID NO 4
<211> LENGTH: 258
<212> TYPE: PRT
<213> ORGANISM: Isochrysis galbana

<400> SEQUENCE: 4

Met Ala Leu Ala Asn Asp Ala Gly Glu Arg Ile Trp Ala Ala Val Thr
  1               5                  10                  15

Asp Pro Glu Ile Leu Ile Gly Thr Phe Ser Tyr Leu Leu Leu Lys Pro
                 20                  25                  30

Leu Leu Arg Asn Ser Gly Leu Val Asp Glu Lys Lys Gly Ala Tyr Arg
             35                  40                  45

Thr Ser Met Ile Trp Tyr Asn Val Leu Leu Ala Leu Phe Ser Ala Leu
 50                  55                  60

Ser Phe Tyr Val Thr Ala Thr Ala Leu Gly Trp Asp Tyr Gly Thr Gly
 65                  70                  75                  80

Ala Trp Leu Arg Arg Gln Thr Gly Asp Thr Pro Gln Pro Leu Phe Gln
                 85                  90                  95

Cys Pro Ser Pro Val Trp Asp Ser Lys Leu Phe Thr Trp Thr Ala Lys
                100                 105                 110

Ala Phe Tyr Tyr Ser Lys Tyr Val Glu Tyr Leu Asp Thr Ala Trp Leu
            115                 120                 125

Arg Val Ser Phe Leu Gln Ala Phe His His Phe Gly Ala Pro Trp Asp
130                 135                 140

Val Tyr Leu Gly Ile Arg Leu His Asn Glu Gly Val Trp Ile Phe Met
145                 150                 155                 160

Phe Phe Asn Ser Phe Ile His Thr Ile Met Tyr Thr Tyr Tyr Gly Leu
                165                 170                 175

Thr Ala Ala Gly Tyr Lys Phe Lys Ala Lys Pro Leu Ile Thr Ala Met
            180                 185                 190

Gln Ile Cys Gln Phe Val Gly Gly Phe Leu Leu Val Trp Asp Tyr Ile
        195                 200                 205

Asn Val Pro Cys Phe Asn Ser Asp Lys Gly Lys Leu Phe Ser Trp Ala
210                 215                 220

Phe Asn Tyr Ala Tyr Val Gly Ser Val Phe Leu Leu Phe Cys His Phe
225                 230                 235                 240

Phe Tyr Gln Asp Asn Leu Ala Thr Lys Lys Ser Ala Lys Ala Gly Lys
                245                 250                 255

Gln Leu

<210> SEQ ID NO 5
<211> LENGTH: 1410
<212> TYPE: DNA
<213> ORGANISM: Phaeodactylum tricornutum
<220> FEATURE:
<221> NAME/KEY: CDS
<222> LOCATION: (1)..(1410)
<223> OTHER INFORMATION: delta-5-desaturase

<400> SEQUENCE: 5 atg gct ccg gat gcg gat aag ctt cga caa cgc cag acg act gcg gta      48
Met Ala Pro Asp Ala Asp Lys Leu Arg Gln Arg Gln Thr Thr Ala Val
  1               5                  10                  15
```

```
                                                     -continued gcg aag cac aat gct gct acc ata tcg acg cag gaa cgc ctt tgc agt       96
Ala Lys His Asn Ala Ala Thr Ile Ser Thr Gln Glu Arg Leu Cys Ser
         20                  25                  30 ctg tct tcg ctc aaa ggc gaa gaa gtc tgc atc gac gga atc atc tat      144
Leu Ser Ser Leu Lys Gly Glu Glu Val Cys Ile Asp Gly Ile Ile Tyr
             35                  40                  45 gac ctc caa tca ttc gat cat ccc ggg ggt gaa acg atc aaa atg ttt      192
Asp Leu Gln Ser Phe Asp His Pro Gly Gly Glu Thr Ile Lys Met Phe
 50                  55                  60 ggt ggc aac gat gtc act gta cag tac aag atg att cac ccg tac cat      240
Gly Gly Asn Asp Val Thr Val Gln Tyr Lys Met Ile His Pro Tyr His
 65                  70                  75                  80 acc gag aag cat ttg gaa aag atg aag cgt gtc ggc aag gtg acg gat      288
Thr Glu Lys His Leu Glu Lys Met Lys Arg Val Gly Lys Val Thr Asp
                 85                  90                  95 ttc gtc tgc gag tac aag ttc gat acc gaa ttt gaa cgc gaa atc aaa      336
Phe Val Cys Glu Tyr Lys Phe Asp Thr Glu Phe Glu Arg Glu Ile Lys
            100                 105                 110 cga gaa gtc ttc aag att gtg cga cga ggc aag gat ttc ggt act ttg      384
Arg Glu Val Phe Lys Ile Val Arg Arg Gly Lys Asp Phe Gly Thr Leu
        115                 120                 125 gga tgg ttc ttc cgt gcg ttt tgc tac att gcc att ttc ttc tac ctg      432
Gly Trp Phe Phe Arg Ala Phe Cys Tyr Ile Ala Ile Phe Phe Tyr Leu
    130                 135                 140 cag tac cat tgg gtc acc acg gga acc tct tgg ctg ctg gcc gtg gcc      480
Gln Tyr His Trp Val Thr Thr Gly Thr Ser Trp Leu Leu Ala Val Ala
145                 150                 155                 160 tac gga atc tcc caa gcg atg att ggc atg aat gtc cag cac gat gcc      528
Tyr Gly Ile Ser Gln Ala Met Ile Gly Met Asn Val Gln His Asp Ala
                165                 170                 175 aac cac ggg gcc acc tcc aag cgt ccc tgg gtc aac gac atg cta ggc      576
Asn His Gly Ala Thr Ser Lys Arg Pro Trp Val Asn Asp Met Leu Gly
            180                 185                 190 ctc ggt gcg gat ttt att ggt ggt tcc aag tgg ctc tgg cag gaa caa      624
Leu Gly Ala Asp Phe Ile Gly Gly Ser Lys Trp Leu Trp Gln Glu Gln
        195                 200                 205 cac tgg acc cac cac gct tac acc aat cac gcc gag atg gat ccc gat      672
His Trp Thr His His Ala Tyr Thr Asn His Ala Glu Met Asp Pro Asp
    210                 215                 220 agc ttt ggt gcc gaa cca atg ctc cta ttc aac gac tat ccc ttg gat      720
Ser Phe Gly Ala Glu Pro Met Leu Leu Phe Asn Asp Tyr Pro Leu Asp
225                 230                 235                 240 cat ccc gct cgt acc tgg cta cat cgc ttt caa gca ttc ttt tac atg      768
His Pro Ala Arg Thr Trp Leu His Arg Phe Gln Ala Phe Phe Tyr Met
                245                 250                 255 ccc gtc ttg gct gga tac tgg ttg tcc gct gtc ttc aat cca caa att      816
Pro Val Leu Ala Gly Tyr Trp Leu Ser Ala Val Phe Asn Pro Gln Ile
            260                 265                 270 ctt gac ctc cag caa cgc ggc gca ctt tcc gtc ggt atc cgt ctc gac      864
Leu Asp Leu Gln Gln Arg Gly Ala Leu Ser Val Gly Ile Arg Leu Asp
        275                 280                 285 aac gct ttc att cac tcg cga cgc aag tat gcg gtt ttc tgg cgg gct      912
Asn Ala Phe Ile His Ser Arg Arg Lys Tyr Ala Val Phe Trp Arg Ala
    290                 295                 300 gtg tac att gcg gtg aac gtg att gct ccg ttt tac aca aac tcc ggc      960
Val Tyr Ile Ala Val Asn Val Ile Ala Pro Phe Tyr Thr Asn Ser Gly
305                 310                 315                 320 ctc gaa tgg tcc tgg cgt gtc ttt gga aac atc atg ctc atg ggt gtg     1008
Leu Glu Trp Ser Trp Arg Val Phe Gly Asn Ile Met Leu Met Gly Val
```

-continued

```
                          325                 330                 335
gcg gaa tcg ctc gcg ctg gcg gtc ctg ttt tcg ttg tcg cac aat ttc      1056
Ala Glu Ser Leu Ala Leu Ala Val Leu Phe Ser Leu Ser His Asn Phe
            340                 345                 350 gaa tcc gcg gat cgc gat ccg acc gcc cca ctg aaa aag acg gga gaa      1104
Glu Ser Ala Asp Arg Asp Pro Thr Ala Pro Leu Lys Lys Thr Gly Glu
            355                 360                 365 cca gtc gac tgg ttc aag aca cag gtc gaa act tcc tgc act tac ggt      1152
Pro Val Asp Trp Phe Lys Thr Gln Val Glu Thr Ser Cys Thr Tyr Gly
        370                 375                 380 gga ttc ctt tcc ggt tgc ttc acg gga ggt ctc aac ttt cag gtt gaa      1200
Gly Phe Leu Ser Gly Cys Phe Thr Gly Gly Leu Asn Phe Gln Val Glu
385                 390                 395                 400 cac cac ttg ttc cca cgc atg agc agc gct tgg tat ccc tac att gcc      1248
His His Leu Phe Pro Arg Met Ser Ser Ala Trp Tyr Pro Tyr Ile Ala
                405                 410                 415 ccc aag gtc cgc gaa att tgc gcc aaa cac ggc gtc cac tac gcc tac      1296
Pro Lys Val Arg Glu Ile Cys Ala Lys His Gly Val His Tyr Ala Tyr
            420                 425                 430 tac ccg tgg atc cac caa aac ttt ctc tcc acc gtc cgc tac atg cac      1344
Tyr Pro Trp Ile His Gln Asn Phe Leu Ser Thr Val Arg Tyr Met His
        435                 440                 445 gcg gcc ggg acc ggt gcc aac tgg cgc cag atg gcc aga gaa aat ccc      1392
Ala Ala Gly Thr Gly Ala Asn Trp Arg Gln Met Ala Arg Glu Asn Pro
    450                 455                 460 ttg acc gga cgg gcg taa                                              1410
Leu Thr Gly Arg Ala
465
```

<210> SEQ ID NO 6
<211> LENGTH: 469
<212> TYPE: PRT
<213> ORGANISM: Phaeodactylum tricornutum

<400> SEQUENCE: 6

```
Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
            85                  90                  95

Phe Val Cys Glu Tyr Lys Phe Asp Thr Glu Phe Glu Arg Glu Ile Lys
        100                 105                 110

Arg Glu Val Phe Lys Ile Val Arg Arg Gly Lys Asp Phe Gly Thr Leu
    115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
            165                 170                 175
```

```
Asn His Gly Ala Thr Ser Lys Arg Pro Trp Val Asn Asp Met Leu Gly
            180                 185                 190

Leu Gly Ala Asp Phe Ile Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
        370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 7
<211> LENGTH: 1344
<212> TYPE: DNA
<213> ORGANISM: Ceratodon purpureus
<220> FEATURE:
<221> NAME/KEY: CDS
<222> LOCATION: (1)..(1344)
<223> OTHER INFORMATION: delta-5-desaturase

<400> SEQUENCE: 7 atg gta tta cga gag caa gag cat gag cca ttc ttc att aaa att gat     48
Met Val Leu Arg Glu Gln Glu His Glu Pro Phe Phe Ile Lys Ile Asp
  1               5                  10                  15 gga aaa tgg tgt caa att gac gat gct gtc ctg aga tca cat cca ggt     96
Gly Lys Trp Cys Gln Ile Asp Asp Ala Val Leu Arg Ser His Pro Gly
             20                  25                  30 ggt agt gca att act acc tat aaa aat atg gat gcc act acc gta ttc    144
Gly Ser Ala Ile Thr Thr Tyr Lys Asn Met Asp Ala Thr Thr Val Phe
```

```
                35                  40                  45
cac aca ttc cat act ggt tct aaa gaa gcg tat caa tgg ctg aca gaa    192
His Thr Phe His Thr Gly Ser Lys Glu Ala Tyr Gln Trp Leu Thr Glu
        50                  55                  60 ttg aaa aaa gag tgc cct aca caa gaa cca gag atc cca gat att aag    240
Leu Lys Lys Glu Cys Pro Thr Gln Glu Pro Glu Ile Pro Asp Ile Lys
65                  70                  75                  80 gat gac cca atc aaa gga att gat gat gtg aac atg gga act ttc aat    288
Asp Asp Pro Ile Lys Gly Ile Asp Asp Val Asn Met Gly Thr Phe Asn
                85                  90                  95 att tct gag aaa cga tct gcc caa ata aat aaa agt ttc act gat cta    336
Ile Ser Glu Lys Arg Ser Ala Gln Ile Asn Lys Ser Phe Thr Asp Leu
            100                 105                 110 cgt atg cga gtt cgt gca gaa gga ctt atg gat gga tct cct ttg ttc    384
Arg Met Arg Val Arg Ala Glu Gly Leu Met Asp Gly Ser Pro Leu Phe
        115                 120                 125 tac att aga aaa att ctt gaa aca atc ttc aca att ctt ttt gca ttc    432
Tyr Ile Arg Lys Ile Leu Glu Thr Ile Phe Thr Ile Leu Phe Ala Phe
    130                 135                 140 tac ctt caa tac cac aca tat tat ctt cca tca gct att cta atg gga    480
Tyr Leu Gln Tyr His Thr Tyr Tyr Leu Pro Ser Ala Ile Leu Met Gly
145                 150                 155                 160 gtt gcg tgg caa caa ttg gga tgg tta atc cat gaa ttc gca cat cat    528
Val Ala Trp Gln Gln Leu Gly Trp Leu Ile His Glu Phe Ala His His
                165                 170                 175 cag ttg ttc aaa aac aga tac tac aat gat ttg gcc agc tat ttc gtt    576
Gln Leu Phe Lys Asn Arg Tyr Tyr Asn Asp Leu Ala Ser Tyr Phe Val
            180                 185                 190 gga aac ttt tta caa gga ttc tca tct ggt ggt tgg aaa gag cag cac    624
Gly Asn Phe Leu Gln Gly Phe Ser Ser Gly Gly Trp Lys Glu Gln His
        195                 200                 205 aat gtg cat cac gca gcc aca aat gtt gtt gga cga gac gga gat ctt    672
Asn Val His His Ala Ala Thr Asn Val Val Gly Arg Asp Gly Asp Leu
    210                 215                 220 gat tta gtc cca ttc tat gct aca gtg gca gaa cat ctc aac aat tat    720
Asp Leu Val Pro Phe Tyr Ala Thr Val Ala Glu His Leu Asn Asn Tyr
225                 230                 235                 240 tct cag gat tca tgg gtt atg act cta ttc aga tgg caa cat gtt cat    768
Ser Gln Asp Ser Trp Val Met Thr Leu Phe Arg Trp Gln His Val His
                245                 250                 255 tgg aca ttc atg tta cca ttc ctc cgt ctc tcg tgg ctt ctt cag tca    816
Trp Thr Phe Met Leu Pro Phe Leu Arg Leu Ser Trp Leu Leu Gln Ser
            260                 265                 270 atc att ttt gtt agt cag atg cca act cat tat tat gac tat tac aga    864
Ile Ile Phe Val Ser Gln Met Pro Thr His Tyr Tyr Asp Tyr Tyr Arg
        275                 280                 285 aat act gcg att tat gaa cag gtt ggt ctc tct ttg cac tgg gct tgg    912
Asn Thr Ala Ile Tyr Glu Gln Val Gly Leu Ser Leu His Trp Ala Trp
    290                 295                 300 tca ttg ggt caa ttg tat ttc cta ccc gat tgg tca act aga ata atg    960
Ser Leu Gly Gln Leu Tyr Phe Leu Pro Asp Trp Ser Thr Arg Ile Met
305                 310                 315                 320 ttc ttc ctt gtt tct cat ctt gtt gga ggt ttc ctg ctc tct cat gta    1008
Phe Phe Leu Val Ser His Leu Val Gly Gly Phe Leu Leu Ser His Val
                325                 330                 335 gtt act ttc aat cat tat tca gtg gag aag ttt gca ttg agc tcg aac    1056
Val Thr Phe Asn His Tyr Ser Val Glu Lys Phe Ala Leu Ser Ser Asn
            340                 345                 350 atc atg tca aat tac gct tgt ctt caa atc atg acc aca aga aat atg    1104
```

```
Ile Met Ser Asn Tyr Ala Cys Leu Gln Ile Met Thr Thr Arg Asn Met
            355                 360                 365 aga cct gga aga ttc att gac tgg ctt tgg gga ggt ctt aac tat cag       1152
Arg Pro Gly Arg Phe Ile Asp Trp Leu Trp Gly Gly Leu Asn Tyr Gln
        370                 375                 380 att gag cac cat ctt ttc cca acg atg cca cga cac aac ttg aac act       1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac       1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc       1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag       1344
Arg Asn Ile Ala Asn Val Ala Ala Lys Leu Thr Lys Lys Ile Ala
                435                 440                 445

<210> SEQ ID NO 8
<211> LENGTH: 447
<212> TYPE: PRT
<213> ORGANISM: Ceratodon purpureus

<400> SEQUENCE: 8

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
        195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255
```

```
Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
            275                 280                 285

Asn Thr Ala Ile Tyr Glu Gln Val Gly Leu Ser Leu His Trp Ala Trp
            290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
                325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
            355                 360                 365

Arg Pro Gly Arg Phe Ile Asp Trp Leu Trp Gly Gly Leu Asn Tyr Gln
            370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
            435                 440                 445

<210> SEQ ID NO 9
<211> LENGTH: 1443
<212> TYPE: DNA
<213> ORGANISM: Physcomitrella patens
<220> FEATURE:
<221> NAME/KEY: CDS
<222> LOCATION: (1)..(1443)
<223> OTHER INFORMATION: delta-5-desaturase
<220> FEATURE:
<221> NAME/KEY: misc_feature
<222> LOCATION: (317)..(317)
<223> OTHER INFORMATION: k is g or t/u
<220> FEATURE:
<221> NAME/KEY: misc_feature
<222> LOCATION: (361)..(361)
<223> OTHER INFORMATION: r is g or a

<400> SEQUENCE: 9 atg gcg ccc cac tct gcg gat act gct ggg ctc gtg cct tct gac gaa    48
Met Ala Pro His Ser Ala Asp Thr Ala Gly Leu Val Pro Ser Asp Glu
  1               5                  10                  15 ttg agg cta cga acg tcg aat tca aag ggt ccc gaa caa gag caa act    96
Leu Arg Leu Arg Thr Ser Asn Ser Lys Gly Pro Glu Gln Glu Gln Thr
             20                  25                  30 ttg aag aag tac acc ctt gaa gat gtc agc cgc cac aac acc cca gca   144
Leu Lys Lys Tyr Thr Leu Glu Asp Val Ser Arg His Asn Thr Pro Ala
         35                  40                  45 gat tgt tgg ttg gtg ata tgg ggc aaa gtc tac gat gtc aca agc tgg   192
Asp Cys Trp Leu Val Ile Trp Gly Lys Val Tyr Asp Val Thr Ser Trp
     50                  55                  60 att ccc aat cat ccg ggg ggc agt ctc atc cac gta aaa gca ggg cag   240
Ile Pro Asn His Pro Gly Gly Ser Leu Ile His Val Lys Ala Gly Gln
 65                  70                  75                  80 gat tcc act cag ctt ttc gat tcc tat cac ccc ctt tat gtc agg aaa   288
Asp Ser Thr Gln Leu Phe Asp Ser Tyr His Pro Leu Tyr Val Arg Lys
                 85                  90                  95
```

|     |     |
| --- | --- |
| atg ctc gcg aag tac tgt att ggg gaa tka gta ccg tct gct ggt gat<br>Met Leu Ala Lys Tyr Cys Ile Gly Glu Xaa Val Pro Ser Ala Gly Asp<br>           100                 105              110 | 336 |
| gac aag ttt aag aaa gca act ctg rag tat gca gat gcc gaa aat gaa<br>Asp Lys Phe Lys Lys Ala Thr Leu Xaa Tyr Ala Asp Ala Glu Asn Glu<br>           115                 120              125 | 384 |
| gat ttc tat ttg gtt gtg aag caa cga gtt gaa tct tat ttc aag agt<br>Asp Phe Tyr Leu Val Val Lys Gln Arg Val Glu Ser Tyr Phe Lys Ser<br>130                 135                 140 | 432 |
| aac aag ata aac ccc caa att cat cca cat atg atc ctg aag tca ttg<br>Asn Lys Ile Asn Pro Gln Ile His Pro His Met Ile Leu Lys Ser Leu<br>145                 150                 155              160 | 480 |
| ttc att ctt ggg gga tat ttc gcc agt tac tat tta gcg ttc ttc tgg<br>Phe Ile Leu Gly Gly Tyr Phe Ala Ser Tyr Tyr Leu Ala Phe Phe Trp<br>                 165                 170              175 | 528 |
| tct tca agt gtc ctt gtt tct ttg ttt ttc gca ttg tgg atg ggg ttc<br>Ser Ser Ser Val Leu Val Ser Leu Phe Phe Ala Leu Trp Met Gly Phe<br>           180                 185              190 | 576 |
| ttc gca gcg gaa gtc ggc gtg tcg att caa cat gat gga aat cat ggt<br>Phe Ala Ala Glu Val Gly Val Ser Ile Gln His Asp Gly Asn His Gly<br>           195                 200              205 | 624 |
| tca tac act aaa tgg cgt ggc ttt gga tat atc atg gga gcc tcc cta<br>Ser Tyr Thr Lys Trp Arg Gly Phe Gly Tyr Ile Met Gly Ala Ser Leu<br>           210                 215              220 | 672 |
| gat cta gtc gga gcc agt agc ttc atg tgg aga cag caa cac gtt gtg<br>Asp Leu Val Gly Ala Ser Ser Phe Met Trp Arg Gln Gln His Val Val<br>225                 230                 235              240 | 720 |
| gga cat cac tcg ttt aca aat gtg gac aac tac gat cct gat att cgt<br>Gly His His Ser Phe Thr Asn Val Asp Asn Tyr Asp Pro Asp Ile Arg<br>                        245                 250              255 | 768 |
| gtg aaa gat cca gat gtc agg agg gtt gcg acc aca caa cca aga caa<br>Val Lys Asp Pro Asp Val Arg Arg Val Ala Thr Thr Gln Pro Arg Gln<br>           260                 265              270 | 816 |
| tgg tat cat gcg tat cag cat atc tac ctg gca gta tta tat gga act<br>Trp Tyr His Ala Tyr Gln His Ile Tyr Leu Ala Val Leu Tyr Gly Thr<br>           275                 280              285 | 864 |
| cta gct ctt aag agt att ttt cta gat gat ttc ctt gcg tac ttc aca<br>Leu Ala Leu Lys Ser Ile Phe Leu Asp Asp Phe Leu Ala Tyr Phe Thr<br>           290                 295              300 | 912 |
| gga tca att ggc cct gtc aag gtg gcg aaa atg acc ccc ctg gag ttc<br>Gly Ser Ile Gly Pro Val Lys Val Ala Lys Met Thr Pro Leu Glu Phe<br>305                 310                 315              320 | 960 |
| aac atc ttc ttt cag gga aag ctg cta tat gcg ttc tac atg ttc gtg<br>Asn Ile Phe Phe Gln Gly Lys Leu Leu Tyr Ala Phe Tyr Met Phe Val<br>                        325                 330              335 | 1008 |
| ttg cca tct gtg tac ggt gtt cac tcc gga gga act ttc ttg gca cta<br>Leu Pro Ser Val Tyr Gly Val His Ser Gly Gly Thr Phe Leu Ala Leu<br>           340                 345              350 | 1056 |
| tat gtg gct tct cag ctc att aca ggt tgg atg tta gct ttt ctt ttt<br>Tyr Val Ala Ser Gln Leu Ile Thr Gly Trp Met Leu Ala Phe Leu Phe<br>           355                 360              365 | 1104 |
| caa gta gca cat gtc gtg gat gat gtt gca ttt cct aca cca gaa ggt<br>Gln Val Ala His Val Val Asp Asp Val Ala Phe Pro Thr Pro Glu Gly<br>           370                 375              380 | 1152 |
| ggg aag gtg aag gga gga tgg gct gca atg cag gtt gca aca act acg<br>Gly Lys Val Lys Gly Gly Trp Ala Ala Met Gln Val Ala Thr Thr Thr<br>385                 390                 395              400 | 1200 |
| gat ttc agt cca cgc tca tgg ttc tgg ggt cat gtc tct gga gga tta<br>Asp Phe Ser Pro Arg Ser Trp Phe Trp Gly His Val Ser Gly Gly Leu | 1248 |

-continued

```
                        405                 410                 415
aac aac caa att gag cat cat ctg ttt cca gga gtg tgc cat gtt cat    1296
Asn Asn Gln Ile Glu His His Leu Phe Pro Gly Val Cys His Val His
                420                 425                 430 tat cca gcc att cag cct att gtc gag aag acg tgc aag gaa ttc gat    1344
Tyr Pro Ala Ile Gln Pro Ile Val Glu Lys Thr Cys Lys Glu Phe Asp
                435                 440                 445 gtg cct tat gta gcc tac cca act ttt tgg act gcg ttg aga gcc cac    1392
Val Pro Tyr Val Ala Tyr Pro Thr Phe Trp Thr Ala Leu Arg Ala His
        450                 455                 460 ttt gcg cat ttg aaa aag gtt gga ttg aca gag ttt cgg ctc gat ggc    1440
Phe Ala His Leu Lys Lys Val Gly Leu Thr Glu Phe Arg Leu Asp Gly
465                 470                 475                 480 tga                                                                 1443
```

<210> SEQ ID NO 10
<211> LENGTH: 480
<212> TYPE: PRT
<213> ORGANISM: Physcomitrella patens
<220> FEATURE:
<221> NAME/KEY: misc_feature
<222> LOCATION: (106)..(106)
<223> OTHER INFORMATION: Xaa is unknown or other
<220> FEATURE:
<221> NAME/KEY: misc_feature
<222> LOCATION: (121)..(121)
<223> OTHER INFORMATION: Xaa is unknown or other

<400> SEQUENCE: 10

```
Met Ala Pro His Ser Ala Asp Thr Ala Gly Leu Val Pro Ser Asp Glu
  1               5                  10                  15

Leu Arg Leu Arg Thr Ser Asn Ser Lys Gly Pro Glu Gln Glu Gln Thr
             20                  25                  30

Leu Lys Lys Tyr Thr Leu Glu Asp Val Ser Arg His Asn Thr Pro Ala
         35                  40                  45

Asp Cys Trp Leu Val Ile Trp Gly Lys Val Tyr Asp Val Thr Ser Trp
     50                  55                  60

Ile Pro Asn His Pro Gly Gly Ser Leu Ile His Val Lys Ala Gly Gln
 65                  70                  75                  80

Asp Ser Thr Gln Leu Phe Asp Ser Tyr His Pro Leu Tyr Val Arg Lys
                 85                  90                  95

Met Leu Ala Lys Tyr Cys Ile Gly Glu Xaa Val Pro Ser Ala Gly Asp
            100                 105                 110

Asp Lys Phe Lys Lys Ala Thr Leu Xaa Tyr Ala Asp Ala Glu Asn Glu
        115                 120                 125

Asp Phe Tyr Leu Val Val Lys Gln Arg Val Glu Ser Tyr Phe Lys Ser
    130                 135                 140

Asn Lys Ile Asn Pro Gln Ile His Pro His Met Ile Leu Lys Ser Leu
145                 150                 155                 160

Phe Ile Leu Gly Gly Tyr Phe Ala Ser Tyr Tyr Leu Ala Phe Trp
                165                 170                 175

Ser Ser Ser Val Leu Val Ser Leu Phe Phe Ala Leu Trp Met Gly Phe
            180                 185                 190

Phe Ala Ala Glu Val Gly Val Ser Ile Gln His Asp Gly Asn His Gly
        195                 200                 205

Ser Tyr Thr Lys Trp Arg Gly Phe Gly Tyr Ile Met Gly Ala Ser Leu
    210                 215                 220

Asp Leu Val Gly Ala Ser Ser Phe Met Trp Arg Gln Gln His Val Val
```

```
                    225                 230                 235                 240
Gly His His Ser Phe Thr Asn Val Asp Asn Tyr Asp Pro Asp Ile Arg
                245                 250                 255
Val Lys Asp Pro Asp Val Arg Arg Val Ala Thr Thr Gln Pro Arg Gln
            260                 265                 270
Trp Tyr His Ala Tyr Gln His Ile Tyr Leu Ala Val Leu Tyr Gly Thr
        275                 280                 285
Leu Ala Leu Lys Ser Ile Phe Leu Asp Asp Phe Leu Ala Tyr Phe Thr
    290                 295                 300
Gly Ser Ile Gly Pro Val Lys Val Ala Lys Met Thr Pro Leu Glu Phe
305                 310                 315                 320
Asn Ile Phe Phe Gln Gly Lys Leu Leu Tyr Ala Phe Tyr Met Phe Val
                325                 330                 335
Leu Pro Ser Val Tyr Gly Val His Ser Gly Gly Thr Phe Leu Ala Leu
            340                 345                 350
Tyr Val Ala Ser Gln Leu Ile Thr Gly Trp Met Leu Ala Phe Leu Phe
        355                 360                 365
Gln Val Ala His Val Val Asp Asp Val Ala Phe Pro Thr Pro Glu Gly
    370                 375                 380
Gly Lys Val Lys Gly Gly Trp Ala Ala Met Gln Val Ala Thr Thr Thr
385                 390                 395                 400
Asp Phe Ser Pro Arg Ser Trp Phe Trp Gly His Val Ser Gly Gly Leu
                405                 410                 415
Asn Asn Gln Ile Glu His His Leu Phe Pro Gly Val Cys His Val His
            420                 425                 430
Tyr Pro Ala Ile Gln Pro Ile Val Glu Lys Thr Cys Lys Glu Phe Asp
        435                 440                 445
Val Pro Tyr Val Ala Tyr Pro Thr Phe Trp Thr Ala Leu Arg Ala His
    450                 455                 460
Phe Ala His Leu Lys Lys Val Gly Leu Thr Glu Phe Arg Leu Asp Gly
465                 470                 475                 480

<210> SEQ ID NO 11
<211> LENGTH: 29
<212> TYPE: DNA
<213> ORGANISM: Artificial sequence
<220> FEATURE:
<223> OTHER INFORMATION: Primer EDELTA8BamF

<400> SEQUENCE: 11
atggatccac catgaagtca aagcgccaa                                           29

<210> SEQ ID NO 12
<211> LENGTH: 26
<212> TYPE: DNA
<213> ORGANISM: Artificial sequence
<220> FEATURE:
<223> OTHER INFORMATION: Primer EDELTA8XhoR

<400> SEQUENCE: 12
atctcgagtt atagagcctt ccccgc                                              26

<210> SEQ ID NO 13
<211> LENGTH: 25
<212> TYPE: PRT
<213> ORGANISM: Artificial sequence
<220> FEATURE:
<223> OTHER INFORMATION: The first 25 amino acid residues of LARS
      delta-8-desaturase
```

```
<400> SEQUENCE: 13

Met Lys Ser Lys Arg Gln Ala Leu Pro Leu Thr Ile Asp Gly Thr Thr
 1               5                  10                  15

Tyr Asp Val Ser Ala Trp Val Asn Phe
            20                  25

<210> SEQ ID NO 14
<211> LENGTH: 25
<212> TYPE: PRT
<213> ORGANISM: Artificial sequence
<220> FEATURE:
<223> OTHER INFORMATION: The first 25 amino acid residues of
      delta-8-desaturase described by Wallis & Browse (ABB 1999)

<400> SEQUENCE: 14

Met Lys Ser Lys Arg Gln Ala Leu Ser Pro Leu Gln Leu Met Glu Gln
 1               5                  10                  15

Thr Tyr Asp Val Ser Ala Trp Val Asn
            20                  25

<210> SEQ ID NO 15
<211> LENGTH: 24
<212> TYPE: PRT
<213> ORGANISM: Artificial sequence
<220> FEATURE:
<223> OTHER INFORMATION: The first 25 amino acid residues of
      delta-8-desaturase as given in GenBank AAD45877

<400> SEQUENCE: 15

Met Lys Ser Lys Arg Gln Ala Leu Ser Pro Leu Gln Leu Met Glu Gln
 1               5                  10                  15

Thr Tyr Asp Val Val Asn Phe His
            20

<210> SEQ ID NO 16
<211> LENGTH: 60
<212> TYPE: DNA
<213> ORGANISM: Artificial sequence
<220> FEATURE:
<223> OTHER INFORMATION: Primer

<400> SEQUENCE: 16
gtcgacccgc ggactagtgg gccctctaga cccgggggat ccggatctgc tggctatgaa      60
```